US009347878B2

(12) United States Patent
Weidmann et al.

(10) Patent No.: US 9,347,878 B2
(45) Date of Patent: May 24, 2016

(54) METHOD AND APPARATUS FOR EXTERNAL CAVITY LASER ABSORPTION SPECTROSCOPY

(71) Applicant: THE SCIENCE AND TECHNOLOGY FACILITIES COUNCIL, Didcot, Oxfordshire (GB)

(72) Inventors: Damien Weidmann, Didcot (GB); Richard Brownsword, Didcot (GB)

(73) Assignee: THE SCIENCE AND TECHNOLOGY FACILITIES COUNCIL, Didcot, Oxfordshire (GB)

( * ) Notice: Subject to any disclaimer, the term of this patent is extended or adjusted under 35 U.S.C. 154(b) by 0 days.

(21) Appl. No.: 14/422,924

(22) PCT Filed: Aug. 9, 2013

(86) PCT No.: PCT/GB2013/052138
§ 371 (c)(1),
(2) Date: Feb. 20, 2015

(87) PCT Pub. No.: WO2014/029971
PCT Pub. Date: Feb. 27, 2014

(65) Prior Publication Data
US 2015/0226665 A1    Aug. 13, 2015

(30) Foreign Application Priority Data

Aug. 21, 2012    (GB) .................................... 1214899.5

(51) Int. Cl.
*G01N 21/00*    (2006.01)
*G01N 21/39*    (2006.01)
(Continued)

(52) U.S. Cl.
CPC . *G01N 21/39* (2013.01); *G01J 3/42* (2013.01); *G01N 21/3504* (2013.01);
(Continued)

(58) Field of Classification Search
CPC .......................... G01N 21/00; G01N 2021/396
USPC .......................................................... 356/437
See application file for complete search history.

(56) References Cited

U.S. PATENT DOCUMENTS 5,780,843 A * 7/1998 Cliche ....................... G01J 3/10
250/205
5,917,188 A 6/1999 Atkinson et al.
(Continued)

FOREIGN PATENT DOCUMENTS

EP    0 196 856    10/1986
WO    WO 00/09536    2/2000

OTHER PUBLICATIONS

Baev et al., "Laser intracavity absorption spectroscopy," Applied Physics B—Lasers and Optics, vol. 69, (1999), pp. 171-202.
(Continued)

*Primary Examiner* — Roy M Punnoose
(74) *Attorney, Agent, or Firm* — Preti Flaherty Beliveau & Pachios LLP

(57) ABSTRACT

Method and apparatus for external cavity laser absorption spectroscopy There is disclosed an apparatus, and corresponding methods, for determining one or more characteristics of a sample in an absorption cell using laser absorption spectroscopy. For example, the characteristic may be concentration of a species in the sample. The apparatus comprises an external cavity semiconductor laser comprising a semiconductor gain medium within an optical resonator. The absorption cell is located within the optical resonator of the external cavity semiconductor laser so as to be optically coupled with the gain medium. A controller is arranged to provide a varied injection current to the semiconductor gain medium. A photodetector is arranged to detect laser light output by the external cavity semiconductor laser. An analyzer is arranged to determine one or more characteristics of the sample from behavior of the detected laser light output as a function of the varied injection current.

23 Claims, 25 Drawing Sheets

(51) Int. Cl.
*G01J 3/42* (2006.01)
*G01N 21/3504* (2014.01)

(52) U.S. Cl.
CPC .... *G01J 2003/423* (2013.01); *G01N 2021/396* (2013.01); *G01N 2201/022* (2013.01); *G01N 2201/06113* (2013.01)

(56) References Cited

U.S. PATENT DOCUMENTS

| | | | |
|---|---|---|---|
| 6,275,288 B1 | 8/2001 | Atkinson et al. | |
| 7,424,042 B2 | 9/2008 | Day et al. | |
| 7,679,059 B2 * | 3/2010 | Zhou | G01J 3/02 250/339.13 |
| 7,733,924 B2 * | 6/2010 | Wysocki | B82Y 20/00 372/20 |
| 7,826,503 B2 | 11/2010 | Day et al. | |
| 2002/0191652 A1 | 12/2002 | Ema | |
| 2007/0047599 A1 * | 3/2007 | Wysocki | B82Y 20/00 372/20 |
| 2007/0121687 A1 | 5/2007 | Amantea | |
| 2012/0062895 A1 | 3/2012 | Rao | |
| 2012/0113426 A1 | 5/2012 | Rao | |
| 2013/0195131 A1 | 8/2013 | Taubman et al. | |
| 2014/0204382 A1 * | 7/2014 | Christensen | G01N 21/39 356/402 |

OTHER PUBLICATIONS

Grossmann, et al., "Low-threshold conical microcavity dye lasers," Applied Physics Letters, AIP, American Institute of Physics, Melville, NY, vol. 97, No. 6, Aug. 12, 2010, p. 63304.

Kosterev et al., "Application of quantum cascade lasers to trace gas analysis," Applied Physics B—Lasers and Optics, vol. 90, (2008), pp. 165-176.

Gurlit et al., "Intracavity diode laser for atmospheric field measurements," Infrared Physics & Technology, vol. 37 (1996) pp. 95-98.

Medhi et al., "Intravacity laser absorption spectroscopy using mid-IR quantum cascade laser," Proc. SPIE 8032, 8032E (2011).

Gensty et al., "Semiclassical model for the relative intensity noise of intersubband quantum cascade lasers," Elsevier, Optics Communications, vol. 256 (2005), pp. 171-183.

Phillips et al., "Intracavity sensing via compliance voltage in an external cavity quantum cascade laser," Optical Society of America, Optics Letters, vol. 37, No. 13, Jul. 1, 2012, p. 2664.

* cited by examiner

METHOD AND APPARATUS FOR EXTERNAL CAVITY LASER ABSORPTION SPECTROSCOPY

The present invention relates to laser absorption spectroscopy, for example to determine the concentration of a species in a sample contained within an absorption cell. In particular, but not exclusively, the invention relates to the use of an external cavity quantum cascade laser for such purposes.

INTRODUCTION

It is known to modulate the wavelength of a tunable laser such as an external cavity quantum cascade laser to detect a species such as a trace gas by absorption spectroscopy, for example see US2012/0113426. This publication notes that as the laser is tuned across an absorption transition, the transmitted laser intensity is a function of Beer's law in which the reciprocal of the transmitted intensity varies as an exponential of the absorption coefficient and a path length through the sample. The application of quantum cascade lasers to trace gas analysis is also discussed in A. Kosterev et al, Appl. Phys. B, volume 90, number 2 (2008) pages 165-176.

Arrangements and techniques for absorption spectroscopy in which the sample is located within the optical cavity of the laser are often referred to using terms such as intra cavity laser absorption spectroscopy, and are described for example in V. M. Baev et al., Appl. Phys. B, 69, 171-202 (1999), W. Gurlit et al., Infrared Physics & Technology, 37, 95-98 (1996), and G. Medhi et al., Proc. SPIE 8032, 8032E (2011).

It would be desirable to address the limitations of the related prior art, for example to improve the sensitivity of absorption spectroscopy techniques.

SUMMARY OF THE INVENTION

The invention provides for the determination of one or more characteristics of a sample, for example a gaseous sample in an absorption cell, by locating at least some of the sample within the optical cavity of an external cavity laser having a gain medium, such that the sample gives rise to a loss rate of photons generated in the gain medium. Characteristics of the sample can then be determined from a reduction in photon lifetime of the external cavity laser in the presence of the sample. For example, the reduction in photon lifetime could be detected from behaviour of the external cavity laser with respect to an injection current applied to the gain medium. This behaviour could be a behaviour or measurement of optical output of the laser. Conveniently, the external cavity may include a tuning element so that the resonant frequency of the external cavity laser can be tuned to or scanned across a plurality of wavelengths, so that one or more characteristics of the sample can be determined at each such or across the scanned range of wavelengths.

In particular, the invention provides methods and apparatus arranged to determine one or more characteristics of a sample in an absorption cell within an external cavity laser, by using the effect of the sample on a relationship between injection current used to drive the laser, and the optical output of the laser. By varying the injection current to measure one or more aspects of the relationship between injection current and laser output, increased sensitivity to absorption characteristics of the sample can be achieved. Such characteristics can be determined at multiple wavelengths by suitable tuning of the external cavity laser, to derive absorption spectra of the sample.

According to one aspect, the invention provides an instrument, or more generally apparatus, which is arranged to determine one or more characteristics of a sample introduced into an absorption cell, the apparatus comprising: an external cavity laser comprising a gain medium within an optical resonator or optical cavity; said absorption cell being arranged to locate at least a portion of the sample within the optical resonator of the external cavity laser so that the sample is optically coupled with the gain medium; a control function arranged to provide a time varying injection current to the gain medium; a detector or photo detector arranged to detect laser light output by the external cavity semiconductor laser; and an analyser or analysis function arranged to determine one or more characteristics of the sample from behaviour of the detected laser light output by the external cavity laser as a function of the varied injection current.

The detected light output by the laser may be, for example, a power or intensity of such light, and the light may be filtered or modified in some way before detection. The control and analysis functions may be separate of may be combined or share some aspects of their functionality. For example, the injection current may be controlled dependent upon the detected laser output using a feedback loop, and the characteristics of the sample may be determined at least in part based on one or more signals derived at least in part from operation of such a feedback loop.

Preferably, the external cavity laser comprises a wavelength selector arranged to selectively tune the laser to each of a plurality of wavelengths. The controller may then be arranged to vary the injection current at each selected wavelength, and the analyser may be arranged to determine one or more characteristics of the sample at each selected wavelength from behaviour of the detected laser light output by the external cavity laser as a function of the varied injection current at each selected wavelength. The wavelength selection may be discrete or continuous. If continuous then of course variations of the injection current may be applied sufficiently rapidly that behaviour of the laser output as a function of the varied injection current can be estimated or determined for a suitable wavelength band, for example within such a band in which the behaviour is reasonably consistent to provide meaningful results.

The wavelength selector may be a diffraction grating forming a boundary of the optical resonator, for example a diffraction grating mounted in a first order Littrow configuration with respect to the optical resonator.

The invention may be used to determine various characteristics of a sample introduced into the absorption cell, for example an indication of the presence and/or concentrations of one or more species such as one or more trace gases identified within the sample by the analyser, and/or an absorption spectrum corresponding to the sample over a range of laser wavelengths.

The external cavity laser is preferably an external cavity semiconductor laser, for example a quantum cascade laser.

The analyser may be arranged to determine said one or more characteristics of the sample at least partly from a laser threshold current of said injection current. The laser threshold current may be determined, for example, from a second derivative of the laser output power with respect to the injection current or similar schemes, or in other ways.

The analyser may additionally or alternatively be arranged to determine said one or more characteristics of the sample at least partly from gradient of changes in the detected laser light output by the external cavity semiconductor laser with respect to the injection current as it is varied above a laser threshold current of the laser.

The controller may be arranged to modulate the injection current with a periodic variation. This may then be used to carry out phase sensitive detection of characteristics of the laser light output. The controller may additionally be arranged to ramp the injection current such that the ramp encompasses the concurrent threshold current.

The invention also provides corresponding methods of determining one or more characteristics of a sample, which may be contained within an absorption cell, for example by locating the sample in the optical cavity or optical resonator of an external cavity laser such that the sample is optically coupled with a gain medium of the semiconductor laser, and thereby gives rise to a reduction in photon lifetime within the laser by means of absorption; applying a variable injection current to the gain medium; detecting laser light output by the external cavity laser; and determining said one or more characteristics of the sample from behaviour of the detected laser light as a function of the applied variations in injection current.

BRIEF SUMMARY OF THE DRAWINGS

Embodiments of the invention will now be described, by way of example only, with reference to the drawings of which:

FIG. 7b illustrates a way in which control and analysis functions can be implemented in the arrangement of FIG. 1 or 3 using the injection current signal of FIG. 7a;

DETAILED DESCRIPTION OF EMBODIMENTS

1. Discussion of Apparatus

Figure 1:
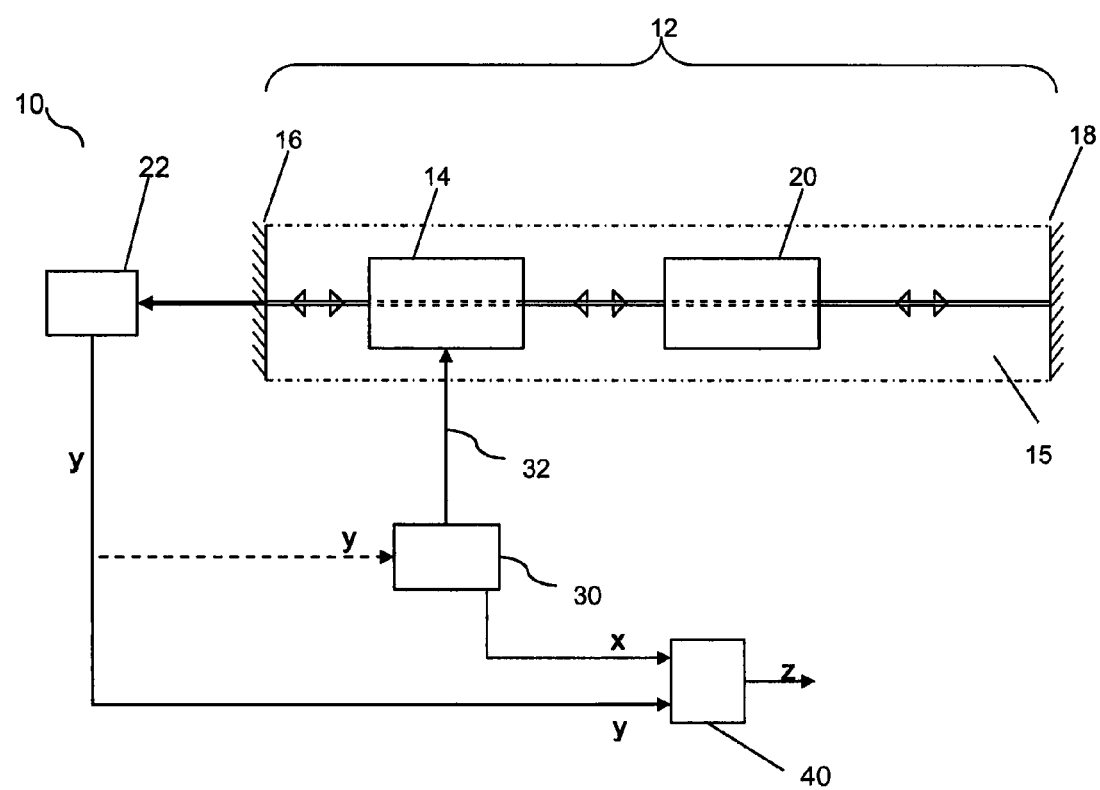
FIG. 1 is a schematic of apparatus for carrying out intra cavity laser absorption spectroscopy according to embodiments of the invention.

Referring now to FIG. 1 there is shown an apparatus 10 for detecting a sample. The apparatus comprises an external cavity semiconductor laser 12 which includes a semiconductor gain medium 14 and an optical resonator defined, for example, by at least partially mirrored surfaces 16, 18. One of these surfaces 16 could, for example, be a polished surface of the gain medium 14 or of a semiconductor element including the gain medium. The sample is typically in gaseous form, and is introduced into or present in an absorption cell 20 which is located within the optical resonator or optical cavity 15 of the external cavity semiconductor laser 12 so as to be optically coupled with the gain medium 14. A photo detector 22 is arranged to detect light generated by the laser 12, for example by coupling to the laser 12 through a partially transmissive one 16 of the reflective surfaces so as to detect intensity or power of light output by the laser 12, and to generate a laser output signal y representative of this intensity or power.

The absorption cell may be of various shapes and sizes, for example being a closed vessel with suitably transparent windows to allow intracavity laser light to pass, and positioned so that the absorption cell intersects the laser light in the optical cavity. In some embodiments the entire optical cavity, including the at least partially mirrored surfaces and the gain medium may be situated within the absorption cell, and in other embodiments less than all or none of these parts may be within the absorption cell, as long as the sample is still present in the optical resonator or cavity to interact with the intracavity laser light.

Depending on the gain characteristics of the gain medium and the optical resonator, a wavelength selective element may be included in or as part of the laser, for example using a diffraction grating as discussed below in a fixed or rotatable configuration.

The apparatus 10 also includes a control unit 30 arranged to deliver a variable and controllable injection current 32 to the laser 12 and in particular to the gain medium 14. The control unit 30 is arranged to output a drive signal x corresponding to the injection current 32, or some proxy for the injection current 32 or some other measure of driving the laser 12 such as temperature of the gain medium 14. As described in more detail below, in some arrangements and modes of operation the injection current 32 may be controlled responsive to the laser output signal y, for example in various types of feedback loops.

An analyser 40 receives the drive signal x and the laser output signal y, and derives from these at least one sample parameter z representing a detected characteristic of the sample from the relationship between x and y as the injection current is varied. Although the laser output signal y is shown as passing directly from the photo detector 22 to the analyser 40, various other implementations are possible, for example in which at least a part of the analyser 40 or analysis function is included within the control unit 30 or control function, and the control and analysis unit and or functions may therefore be combined in various ways. One such example is discussed below in connection with FIGS. 7a and 7b.

The semiconductor gain medium is preferably a multimode or broadband gain medium, and may be implemented, for example, using a quantum cascade laser (QCL) semiconductor device arranged such that the absorption cavity 20 is included in the optical resonator 15 which forms the external cavity laser 12 including the QCL device.

The sample may be a mixture of gases, for example a sample of environmental air, of human or animal breath, or may comprise a single gas for detection. The instrument may output, for example, an absorption spectrum of any such sample at just one wavelength, at a few or many selected wavelengths, or across a wavelength range, or may output related data such as identification or concentration of one or more species identified within the sample from the absorption data. The sample may instead be in liquid form, for example a sample of environmental water or condensate from a gas, or a sample from a human or animal subject such as blood or urine.

Figure 2:
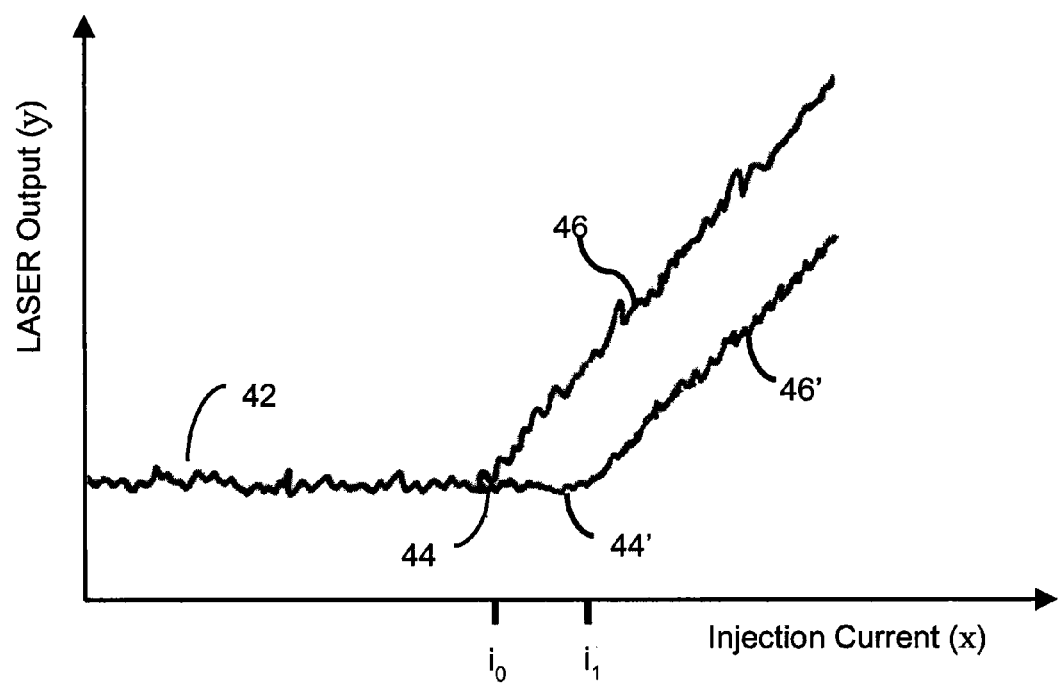
FIG. 2 illustrates a relationship between injection current used to drive the laser of FIG. 1, and the laser optical output.

Referring now to FIG. 2 there is shown a graph representing in general terms a relationship between injection current 32 and detected laser light intensity at the photo detector 22. A similar graph could be presented relating the drive signal x and the laser output signal y, and the consequent shape of such a graph will depend on how these signals are related to the injection current and detected laser light intensity, and could be interpreted accordingly. The graph comprises a plateau region 42 where the injection current is insufficient to cause the gain medium to lase. The degree to which this plateau region 42 represents an above zero laser output intensity, and has a non-zero average gradient will depend on the characteristics of the laser 12, the photo detector 20, and other sources of noise in the apparatus 10. Above a cusp 44 in the graph, which represents a threshold current $i_0$ of the laser 12, the detected intensity rises in an approximately linear manner with increasing injection current, following slope 46.

The inventors have observed that introduction of a sample into absorption cavity 20, or varying the concentration or constitution of such a sample, affects aspects of the graph shown in FIG. 2, in particular if the sample absorbs at a wavelength output by the laser 12 and detected by the photodetector 22. Under the familiar Beer-Lambert law of absorption, the reciprocal of the intensity of light detected at the photodetector would simply vary exponentially with the concentration of the absorber. However, it is observed by the inventors that an absorbing sample also gives rise to an increase in the threshold current of the laser 12. This is illustrated in FIG. 2 as a change in the shape of the graph to have a cusp 44' at higher injection current. The gradient of the slope 46' is also different to that of the slope in absence of the absorber.

In light of the illustrative graph of FIG. 2 it can be seen that the analyser 40 may be arranged to determine one or more characteristics of a sample in the absorption cavity 20 at least partly from a laser threshold current of said injection current, determined for example by varying the injection current and analysing the resulting drive signal x and laser output signal y. Alternatively, or additionally, the analyser 40 may be arranged to determine one or more characteristics of a sample in the absorption cavity 20 at least partly from a gradient of the detected laser light output by the laser 12 as the injection current is varied above the laser threshold current. Of course, combinations of these two and other techniques related to the behaviour of the laser 12 as the injection current is varied may be used.

Figure 3:
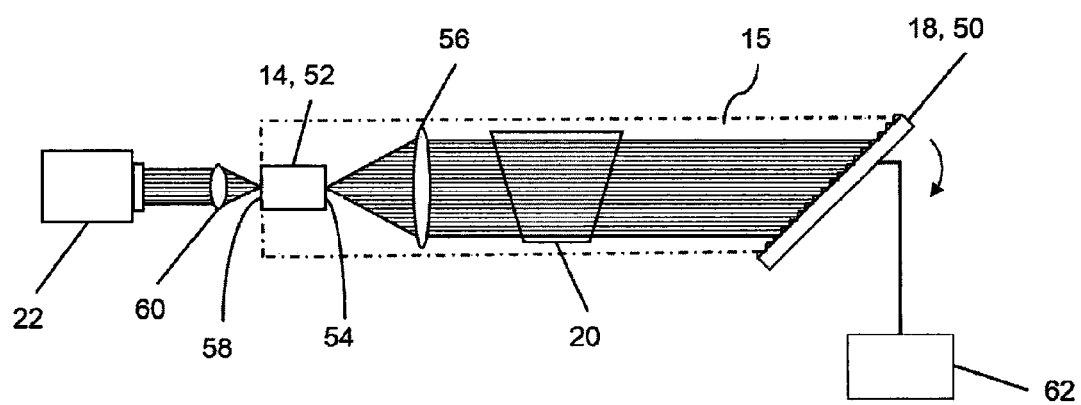
FIG. 3 shows in more detail how aspects of the apparatus of FIG. 1 may be implemented.

In order to determine characteristics of the sample over a range of wavelengths, the apparatus of FIG. 1 may be constructed so that the laser 20 is tuned to scan across or tune to each of a plurality of wavelengths. The photodetector 22 then detects optical output of the laser 12 at or proximal to each of the plurality of wavelengths, and the injection current is varied or modulated at or close to each selected wavelength. To this end, FIG. 3 shows apparatus similar to FIG. 1 in which one of the at least partially reflective surfaces 18 of the optical resonator is implemented as a diffraction grating 50 mounted in a first order Littrow configuration, although various other types of wavelength selective elements familiar to the skilled person may be used. Electrical control, signal handling and analysis elements are omitted for clarity, but may be provided as shown in FIG. 1. The gain medium 14 is provided by a quantum cascade laser (QCL) element in which light emerging from the front facet 54 is collimated by an F1 germanium lens 56 before being directed through the intracavity absorption cell 20 and onto the diffraction grating 50. Radiation from the rear facet 58 of the QCL is collimated and directed to an IR-sensitive photodetector 22 to monitor the QCL output.

The QCL element used is a Maxion type M738. A compact, stable, temperature controlled housing for the QCL element is provided using: spring loaded contacts to supply current to the laser; a hybrid sub-D feedthrough for current for a Peltier temperature controlled element, QCL injection current, and a thermistor temperature sensor; liquid coolant feedthrough to a cooling block with dry quick connects for easy connection; thermal bonding of the QCL element and cooling block using HC thermal epoxy; feedthrough for a internal relative humidity sensor to avoid condensation; and a collimation lens 60 at the rear facet of the QCL element to direct the QCL optical output to the photodetector 22.

The QCL housing is mounted on an XYZ micrometer stage to allow the fine adjustment of the QCL facets to match the optical axis of the optical resonator 15 for effective feedback between the diffraction grating 50 and the QCL element 52.

Figure 4:
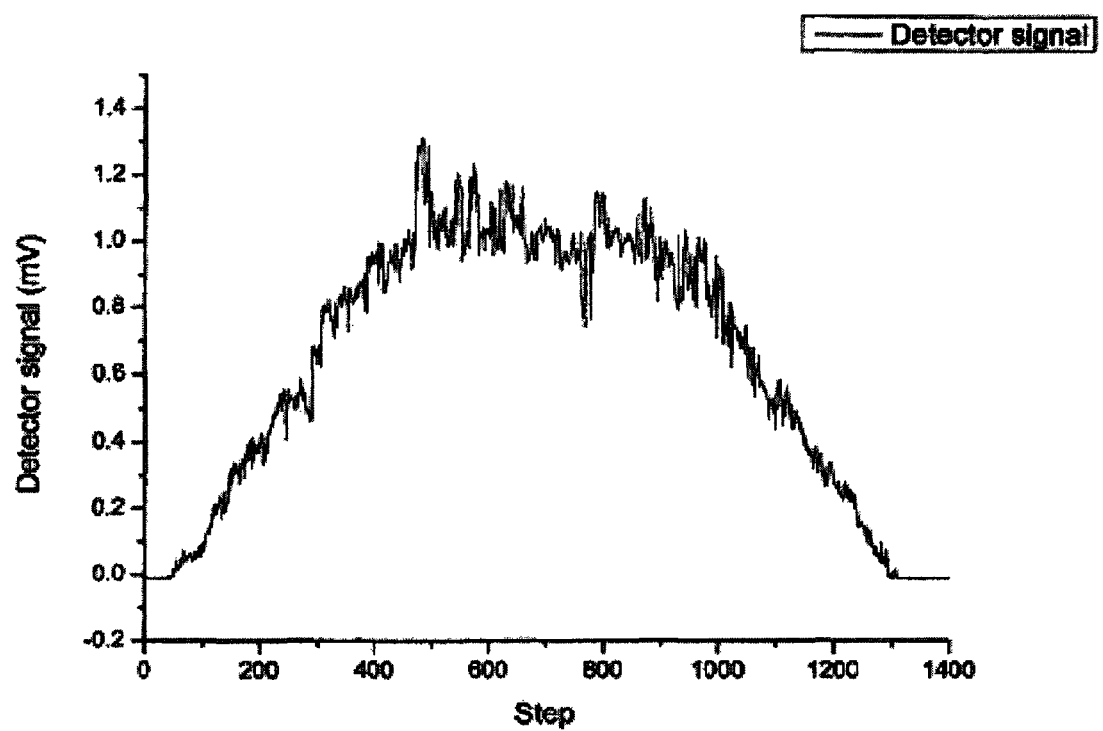
FIG. 4 is a graph of laser optical output of the apparatus of FIG. 3 in which the diffraction grating is rotated through steps (abscissa) corresponding to a plurality of laser wavelengths.
Figure 5:
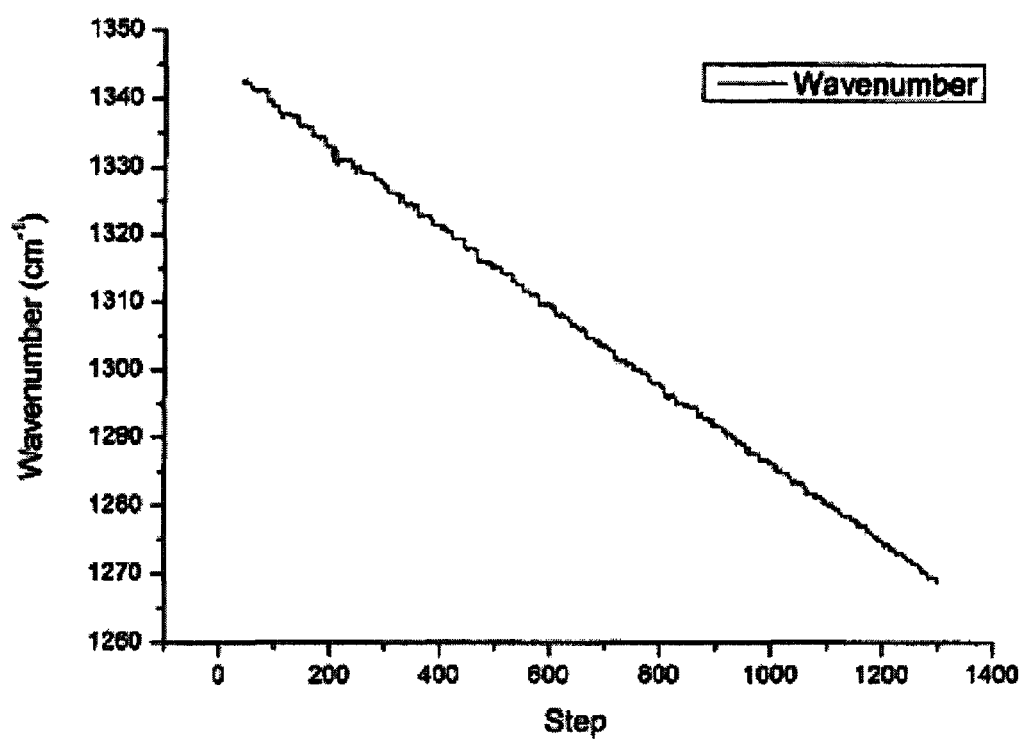
FIG. 5 associates the steps of FIG. 4 with the laser output wavelength expressed in terms of wavenumber.

Wavelength tuning of the laser is achieved by rotation of the grating 50 which is mounted on a compact piezoelectric rotations stage (Newport AG-PR100P). An example of the tuning range and power output of the laser is shown in FIGS. 4 and 5. The laser wavelength was measure by directing the output onto a Bristol model 721 spectrum analyser. Wavelength tuning of the laser is illustrated in general terms in FIG. 3 by wavelength control element 62.

To determine the concentration of component of a sample such as a gas from its absorption spectrum it maybe desirable to measure, in addition, the spectrum in the absence of the absorbing gas (the background). As the wavelength ranges of the two spectra should coincide to make a proper comparison of the two, and the use of a costly and bulky spectrum analyser is undesirable in a deployable instrument, the issue of repeatability of wavelength scans becomes important. A microswitch (Baumer MyCom), which provided a logic transition when activated by rotation of the grating stage, is used in the arrangement of FIG. 3 to define a reference point from which successive wavelength scans may be started. The repeatability achieved over range of about 60 cm$^{-1}$ using the arrangement of FIG. 3 is better than 1%.

Figure 6:
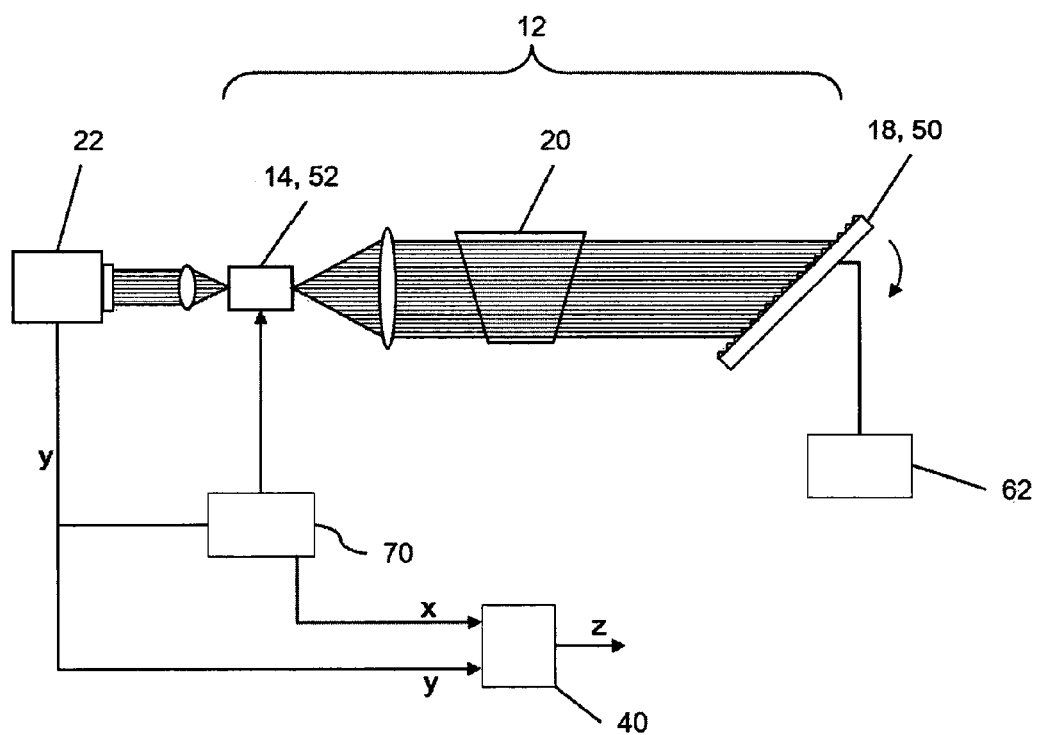
FIG. 6 illustrates a way in which control and analysis functions can be implemented in the arrangement of FIG. 1 or 3.

Some example schemes by which the apparatus of FIG. 1 or 3 can be configured and controlled to determine behaviour of the detected laser light output as a function of the injection current are now discussed. A first such example is illustrated in FIG. 6. In this example, a power signal output from the photo detector, which may be the laser output signal y of FIG. 1, is provided to a constant power feedback loop circuit 70, which may for example be implemented in or as the control unit 30 of FIG. 1. In this example, a change in threshold current induced by the introduction or change of an absorbing sample in the absorption cavity 20, measured at multiple wavelengths, is used to deduce the absorbance profile of the sample as a function of wavelength. The threshold current is taken to be the smallest injection current which produces laser power detectable above the detector noise level. The laser power is used as a control signal applied to the injection current to maintain it at the threshold. Modulation of the injection current and phase sensitive detection could also be used to improve signal to noise ratio and therefore sensitivity. Once a profile of threshold current across a range of wavelengths has been recorded, a fit of the profile to reference spectral data can be used to retrieve a concentration of a species within the sample. Alternatively, a measurement at a single wavelength coinciding with an absorption peak of the species to be detected may be used.

Figure 7A:
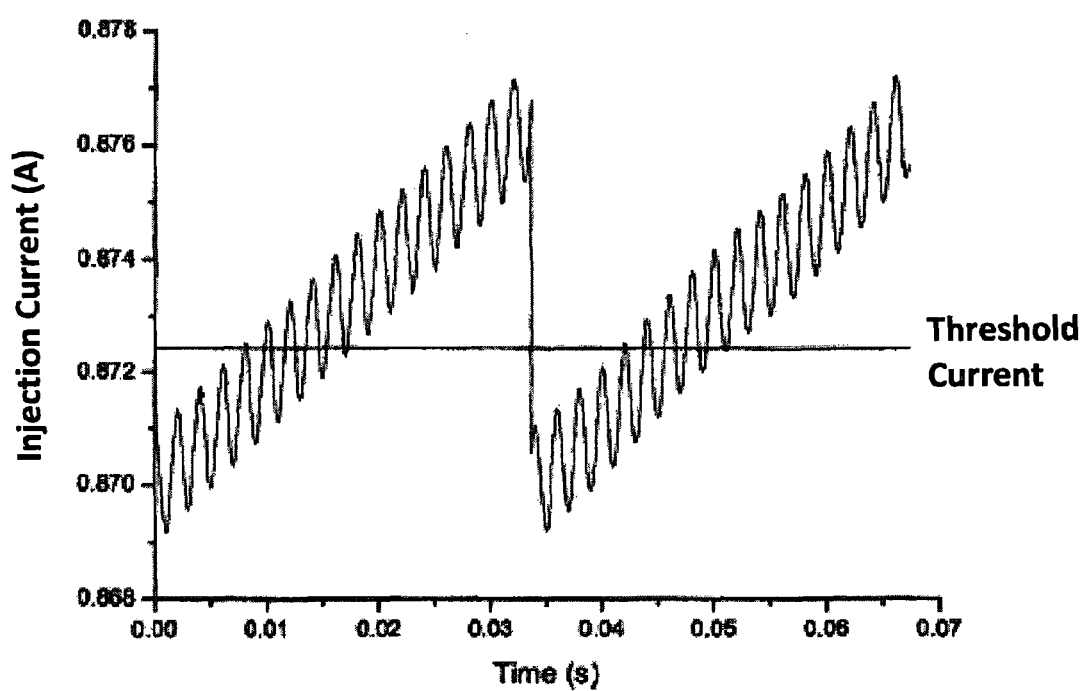
FIG. 7a is a graph of an injection current signal which may be applied to the laser gain medium of the apparatus of FIG. 1 or 3.

In a second such example the injection current 32 is ramped over the threshold current while simultaneously being modulated at a higher frequency. A phase sensitive detection scheme may be used to improve the signal to noise ratio. A suitable driving signal for the injection current 32 under this scheme is illustrated in FIG. 7a, which shows a graph of injection current 32 against time, for a situation in which the threshold current is expected to lie at about 872.5 mA. If necessary, the range of the ramp of injection current may be continuously or periodically adjusted so that the threshold current remains within the ramp range.

Phase sensitive detection can also be used to extract the second derivative of the power, which for a well defined threshold current shows a narrow peak at the threshold current. Peak detection algorithms can be used to determine the threshold current to a high degree of precision. Alternatively, a phase sensitive detection third derivative could be used as a control signal for the injection current to maintain the current threshold at a fixed point, thus providing a direct measure of the threshold current as the wavelength of the laser is scanned.

Figure 7B:
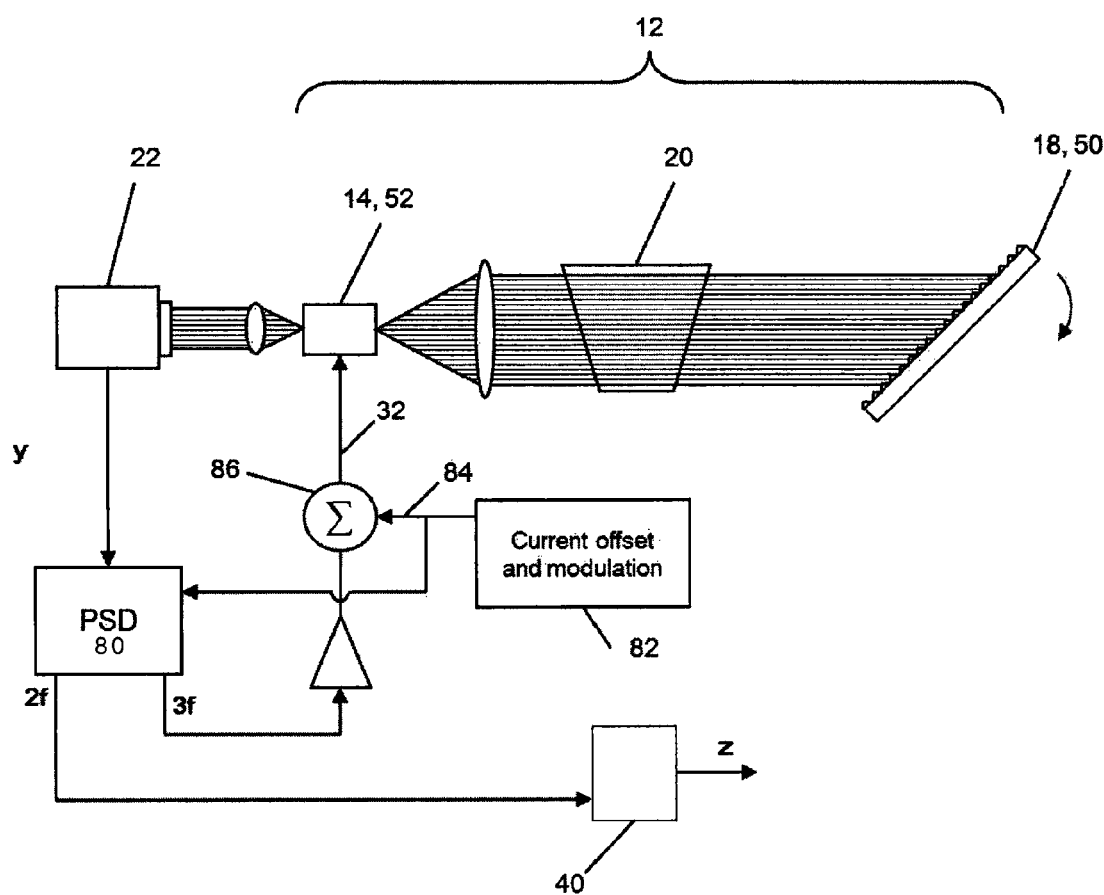

FIG. 7b shows how the apparatus of FIG. 1 or 3 can be implemented using a phase sensitive detection element 80, and a current offset and modulation element 82. The current offset and modulation element 82 provides a modulated driving signal 84 in the form of a current ramp combined with a more rapid modulation, in the form shown in FIG. 7a. The phase sensitive detection element 80 receives this modulated driving signal as a reference, and uses this to output a second order derivative 2f and a third order derivative 3f of the laser output signal y in respect of injection current 32. The third order derivative 3f, which displays positive and negative peaks with a zero intercept at the threshold current, is combined with the modulated driving signal at amplifier 86 to provide an offset which maintains the ramp of the modulated driving signal at a fixed point with respect to the varying threshold current. The threshold current can in turn be read by analyser 40 as a peak in the second derivative 2f of the laser output signal with respect to driving current.

The apparatus described herein may be packaged in various ways. For example, integration of some or all of the components (for example the optical resonator, the absorption cell, the gain medium and the photo detector) onto a single substrate provided with a hollow waveguide structure used to implement the absorption cell, could provide greater stability and reproducibility of the threshold current at a given wavelength. Greater stability would improve the instrument sensitivity. Greater reproducibility would reduce the frequency of calibration needed, thereby increasing the instrument's detection rate.

Further discussion of ways in which the apparatus may be controlled and the data analysed to derive characteristics of the sample is provided in section "4. Data analysis" below.

2. Example Spectral Measurements

Figure 8A:
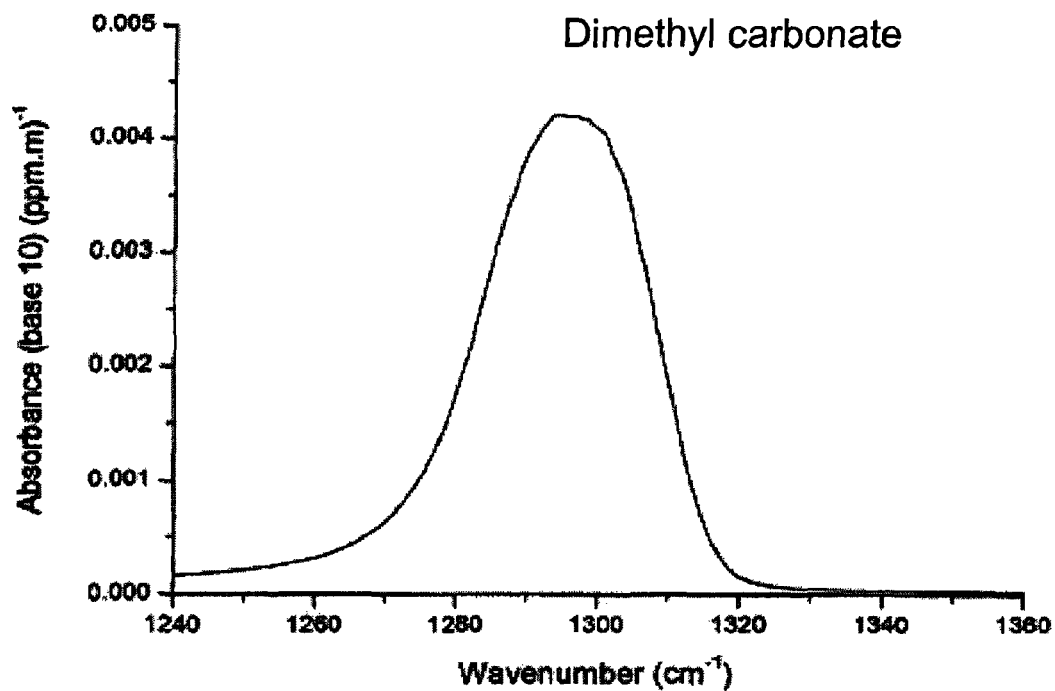
FIGS. 8a and 8b are absorption spectra of dimethyl carbonate and pentafluoroethane respectively.
Figure 8B:
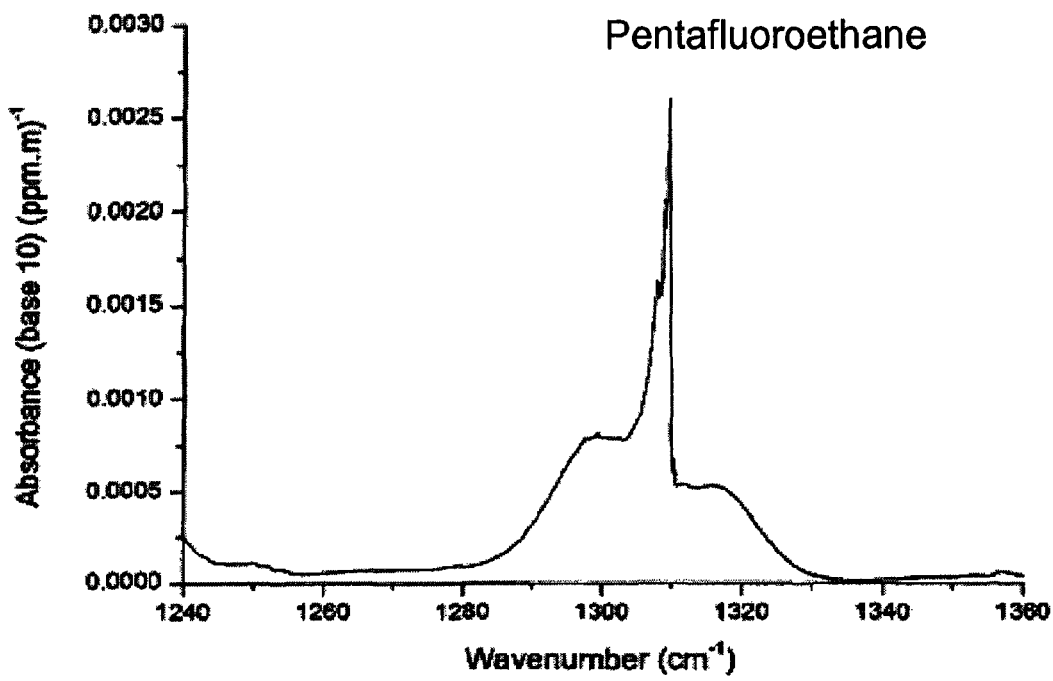

Dimethyl carbonate (DMC) and pentafluoroethane (PFE) were chosen as intracavity absorbers for use as samples in the absorption cavity 20 discussed above. Both have broad-band spectra lying within the 1265-1345 cm$^{-1}$ tuning range of the external cavity QCL 12 at 1100 mA. Their absorption cross-sections in this region are shown in FIGS. 8A and 8B in the 7.5 micron region.

Figure 9A:
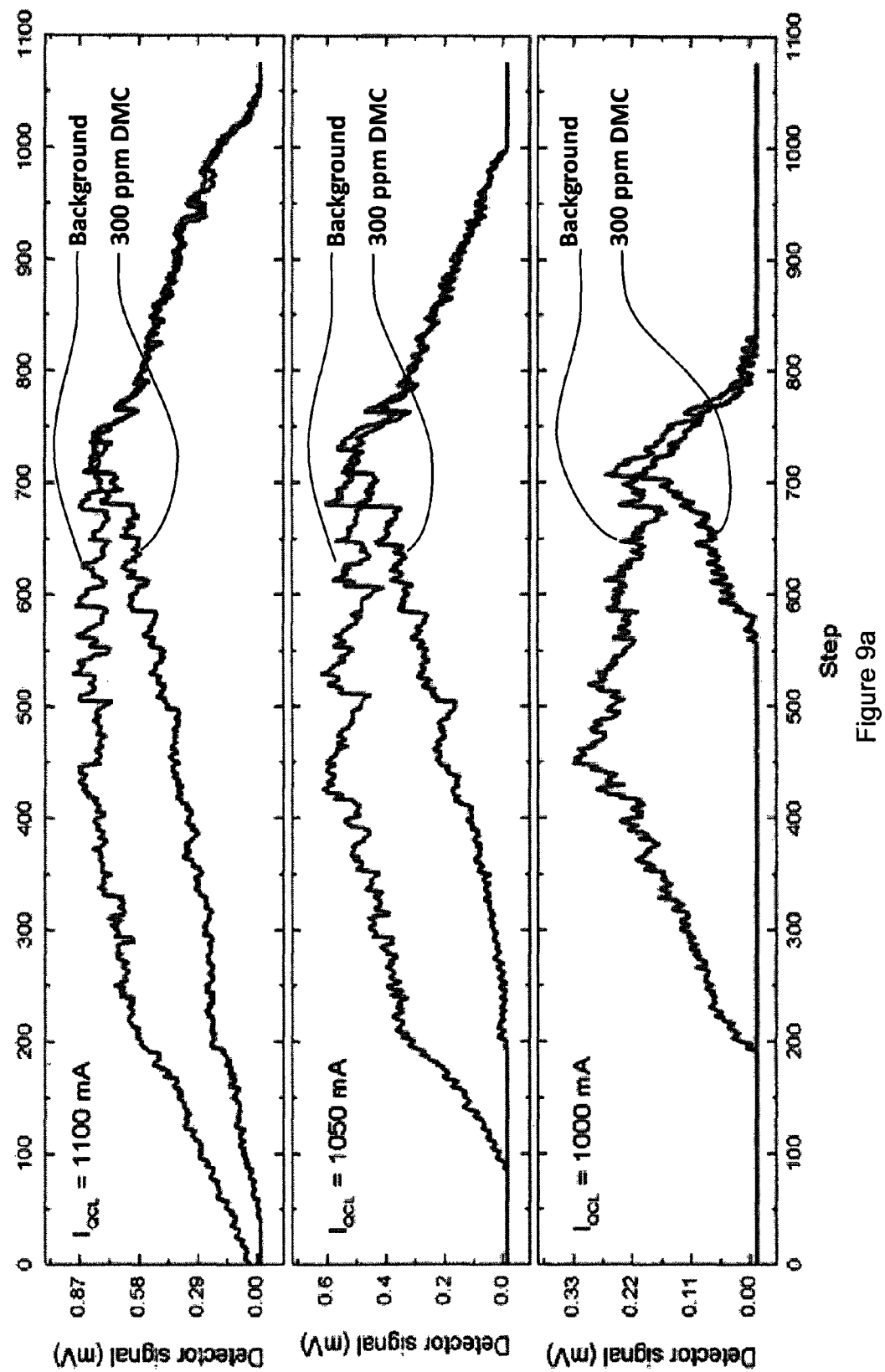
FIG. 9a shows the change in laser optical output of apparatus embodying the invention over a range of wavelengths in the absence of an absorption species ("Background") and in the presence of 300 ppm dimethyl carbonate, for three different laser injection currents.
Figure 9B:
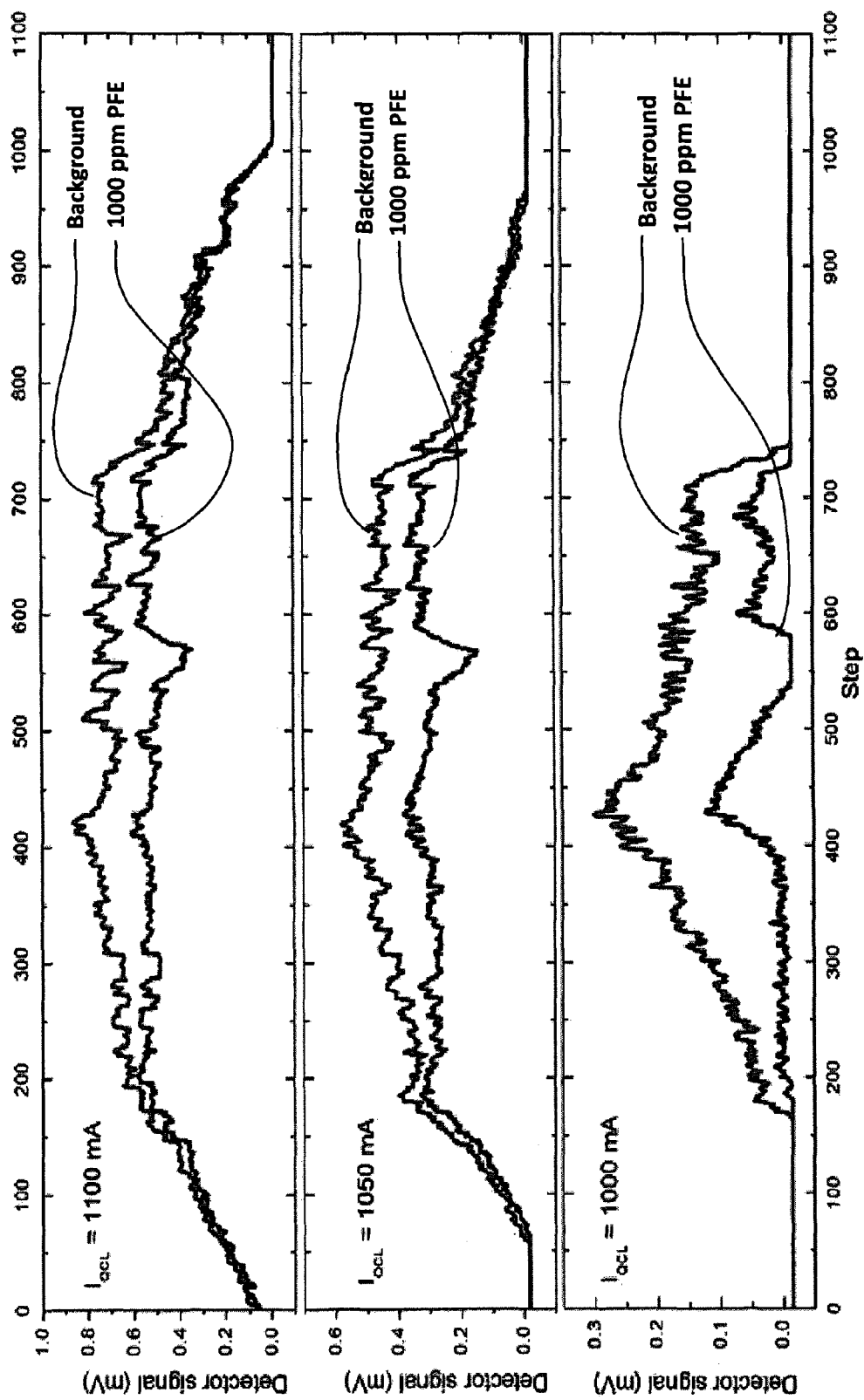
FIG. 9b shows the change in laser optical output of apparatus embodying the invention over a range of wavelengths in the absence of an absorption species ("Background") and in the presence of 1000 ppm polyfluoroethane, for three different laser injection currents.

Intracavity absorption spectra recorded using the external cavity QCL 12 for these two gases are shown in FIG. 9A for 300 ppm DMC and in FIG. 9B for 1000 ppm PFE at three different QCL injection currents IQCL. In each graph the upper curve represents the background signal y in absence of the sample, and the lower curve the detector signal y in the presence of the sample, each across the full range of wavelengths tunable by the laser 12.

Figure 10:
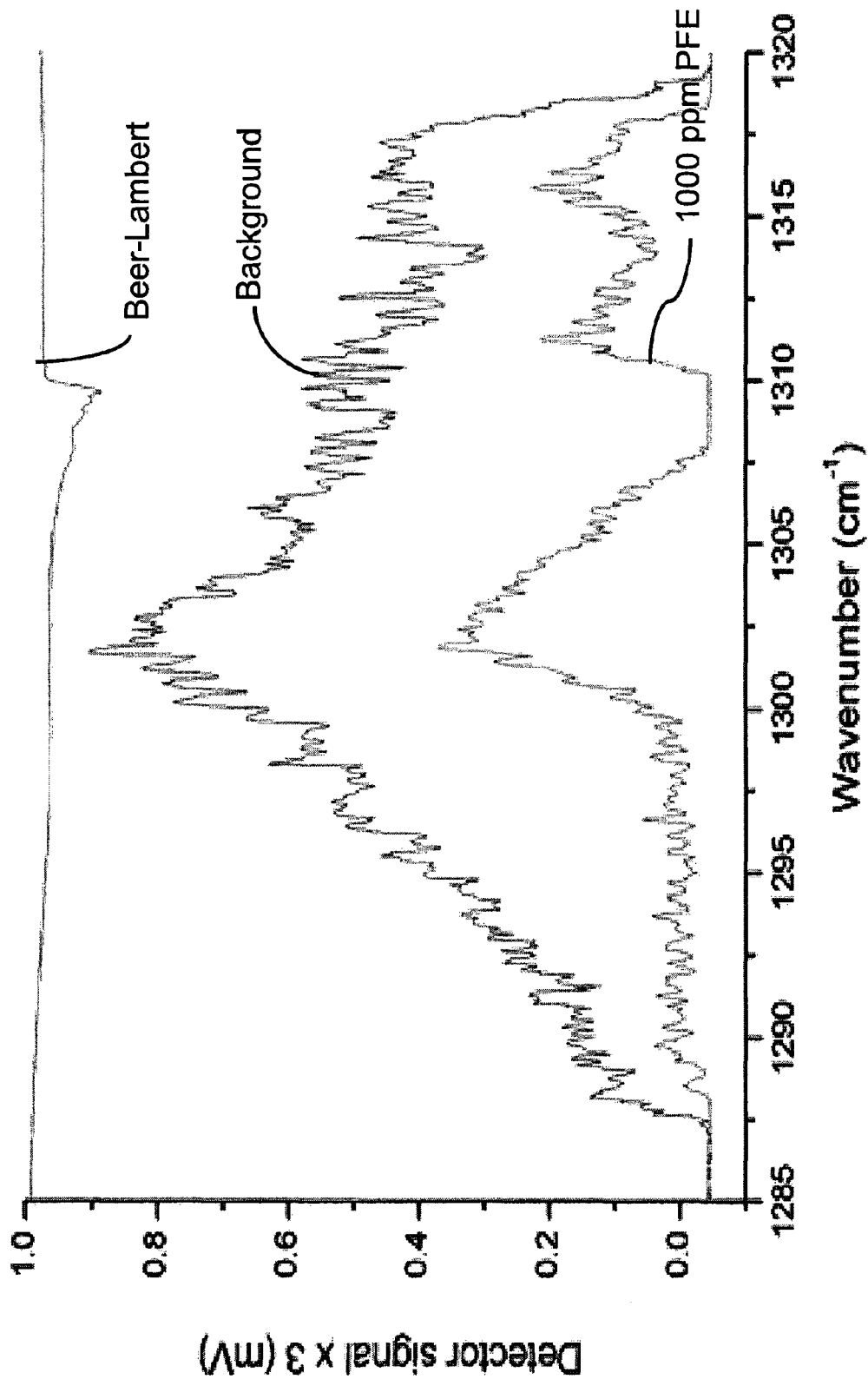
FIG. 10 plots the data of the lower graph of FIG. 9b under the expected shape of an absorption spectrum according to coventional Beer-Lambert absorption.

A wavelength-selective absorption is evident in both cases, especially for PFE for which the strong absorption of the Q-branch at 1310 cm$^{-1}$ is clearly seen. Comparison of the 1000 mA data for PFE of FIG. 9b with an absorption spectrum calculated for Beer-Lambert behaviour is shown in FIG. 10. Compared with the Beer-Lambert absorption curve (top curve in figure), the apparent absorption in our external cavity QCL data (lower two curves) show a greatly enhanced absorption. At 1302 cm$^{-1}$ for example, the Beer-Lambert absorption is ≈3.5% in contrast to the ≈65% observed in our data.

The transmission T for each compound at a given wavenumber may be calculated from the transmitted power:

$$T = \frac{P_{Transmitted}}{P_0}$$

An interesting feature of the spectra for both compounds is the variation of transmission T at a given wavenumber with injection current: as the current is reduced, T decreases sharply, in some cases being reduced to zero. This behaviour is in contrast to the Beer-Lambert behaviour in conventional absorption spectroscopy, in which T is, in the absence of saturation effects, determined solely by the absorption path length, the absorption cross-section of the gas, and the gas concentration. At the mW power levels of the external cavity QCL 12, saturation effects seemed unlikely to be the cause of the non-linear transmission observed. In fact, saturation can be discounted, as the transmission at a given wavelength and injection current is found, as described in the next section, to be dependent on intracavity absorber concentration, whereas the saturation intensity is independent of concentration.

Figure 11:
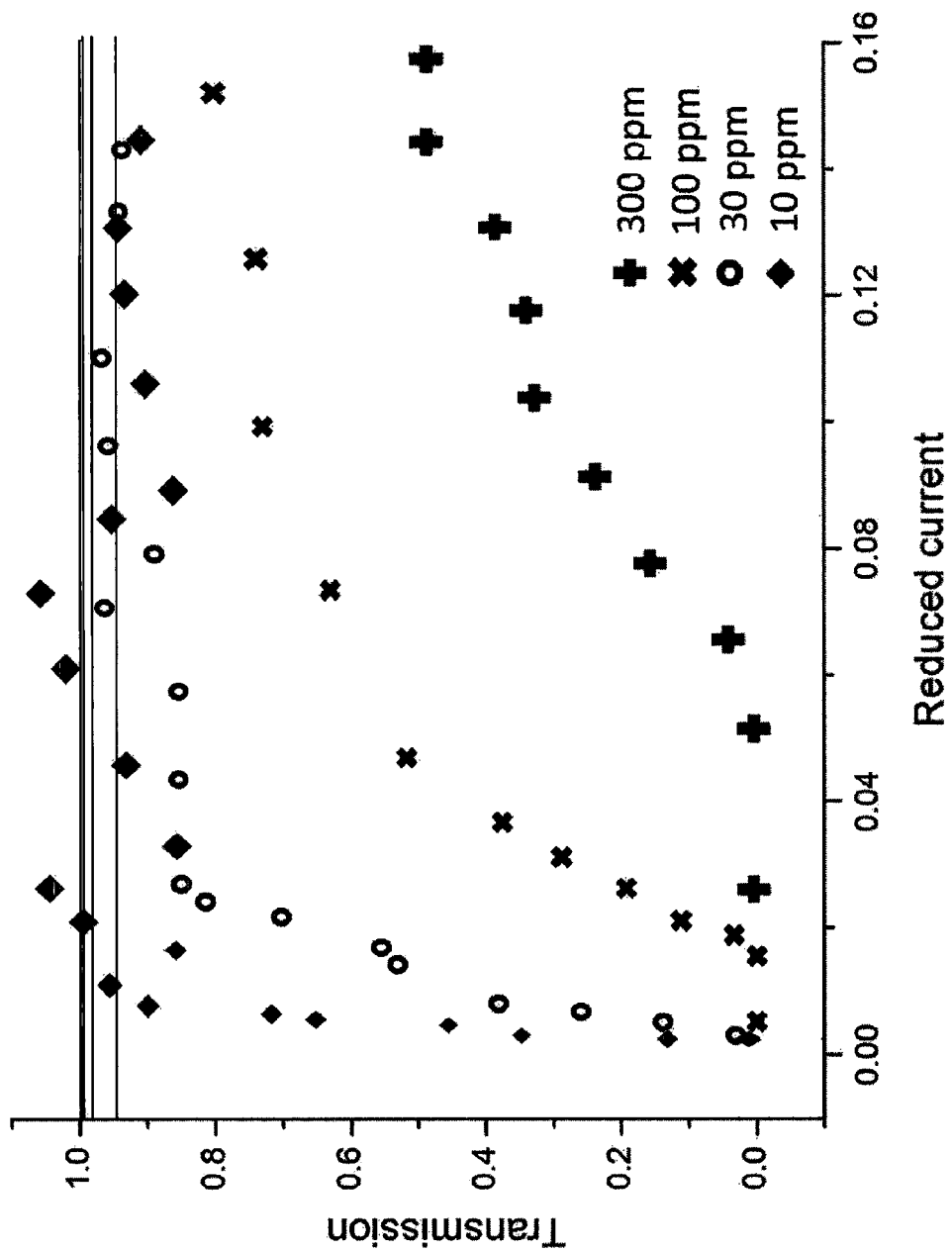
FIG. 11 is a plot of optical transmission of a various concentrations of a dimethyl carbonate sample against reduced current (defined in the text) which is a function of injection current and threshold current of the laser.

Intracavity absorption measurements were made at fixed wavenumber, but varying injection current I and gas concentration N, in order to characterise the behaviour of the intracavity absorption. In each case, the laser output signal was measured with and without an intracavity absorber, and the transmission T calculated as before. Results for DMC for a wavelength of 1300 cm$^{-1}$ are shown in FIG. 11. Data are presented as a function of the reduced current I':

$$I' = \frac{I}{I_{thr}} - 1$$

where $I_{thr}$ is the threshold current for the wavelength employed. The horizontal lines represent the absorption expected from Beer-Lambert behaviour for each concentration, independent of current as previously observed. Note that the enhanced absorptions observed cannot arise simply through an increase of the effective absorption path length in the intracavity cell, as otherwise the enhancement would be independent of injection current.

Figure 12:
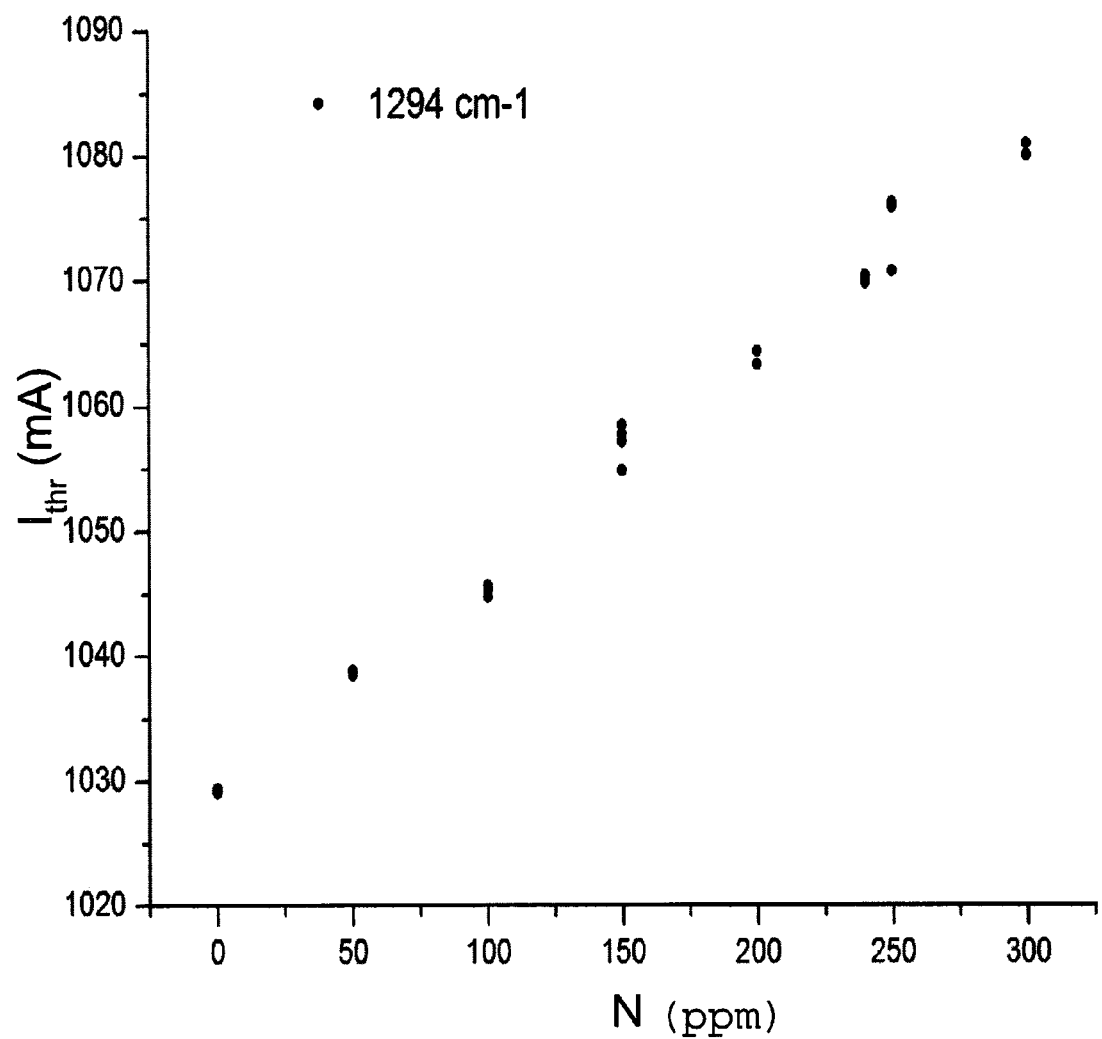
FIG. 12 is a plot of threshold current as a function of concentration of an absorbing species at a laser wavenumber of 1294 $cm^{-1}$.

A further set of intracavity absorption measurements was made, measuring at two different wavelengths the laser threshold current $I_{thr}$ for a range of values of gas concentration N. The results for a wavelength of 1294 cm$^{-1}$ are shown in FIG. 12.

3. Rate Equation Model

The results presented above demonstrate that the enhanced intracavity absorption observed arises from a perturbation of the external cavity laser system itself, rather than an amplification of linear, Beer-Lambert absorption. A rate equation model describing the laser was therefore used in order to gain insight into the effects described.

3.1 Base Model

We adopt the 3-level model of Elsäβer & Gensty (T. Gensty & W. Elsäβer, 'Semiclassical model for the relative intensity noise of intersubband quantum cascade lasers, Optics Communications, 256, 171-183 (2005)). Level 3, the upper laser level, is populated by injection and depopulated by phonon scattering to levels 1 and 2 and stimulated emission. Level 2 is populated by stimulated emission and phonon scattering from level 3, and depopulated by phonon scattering to level 1. Level 1 is populated by phonon scattering from levels 3 and 2, and depopulated by loss to the subsequent miniband. Photons are produced by stimulated and spontaneous emission, and lost through processes such as mirror loss and, in this case, intracavity absorption.

TABLE 1 parameters used in the rate equation base model

| Symbol | Parameter | Value |
|---|---|---|
| $T_{32}$ | Phonon scattering time (3 → 2) | 2.1 ps |
| $T_{31}$ | Phonon scattering time (3 → 1) | 2.6 ps |
| $T_{21}$ | Phonon scattering time (2 → 1) | 0.3 ps |
| $T_e$ | Electron lifetime | 1.16 ps |
| g | Gain coefficient | 140 s$^{-1}$ |
| Z | No. of gain stages | 25 |
| β | Spontaneous emission factor | 10$^{-6}$ |
| $\tau_P$ | Photon lifetime | 250 ps |
| L | Total cavity length | 20 cm |
| l | Length of intracavity cell | 2.5 cm |

The rate equations for the populations Ni of level i and the photon number P are:

$$\frac{dN_3}{dt} = \frac{I_{in}}{q} - \frac{N_3}{\tau_{32}} - \frac{N_3}{\tau_{31}} - g(N_3 - N_2)P$$

$$\frac{dN_2}{dt} = \frac{N_3}{\tau_{32}} - \frac{N_2}{\tau_{21}} + g(N_3 - N_2)P$$

$$\frac{dN_1}{dt} = \frac{N_3}{\tau_{31}} + \frac{N_2}{\tau_{21}} - \frac{I_{in}}{q}$$

$$\frac{dP}{dt} = Zg(N_3 - N_2)P + Z\beta\frac{N_3}{\tau_e} - \frac{P}{\tau_P}$$

$I_{in}$ is the injection current and q the charge on the electron. By setting all derivates to zero we obtain for the photon number P:

$$AP^2 + BP + C = 0$$

with $$A = \frac{g}{\tau_P}\left(\frac{1}{\tau_{21}} + \frac{1}{\tau_{31}}\right)$$

$$B = \frac{1}{\tau_P \tau_{21}}\left(\frac{1}{\tau_{32}} + \frac{1}{\tau_{31}}\right) + \frac{I_{in} Z g}{q}\left(\frac{1}{\tau_{32}} - \frac{1}{\tau_{21}} - \frac{\beta}{\tau_e}\right)$$

$$C = -\frac{Z\beta I_{in}}{q\tau_e \tau_{21}}$$

Using the standard solution for a quadratic and setting the condition P=0 at $I_{in}$=0 we obtain for the steady-state photon population:

$$P = \frac{-B + (B^2 - 4AC)^{1/2}}{2A} \quad \text{Eq. 1}$$

Figure 13:
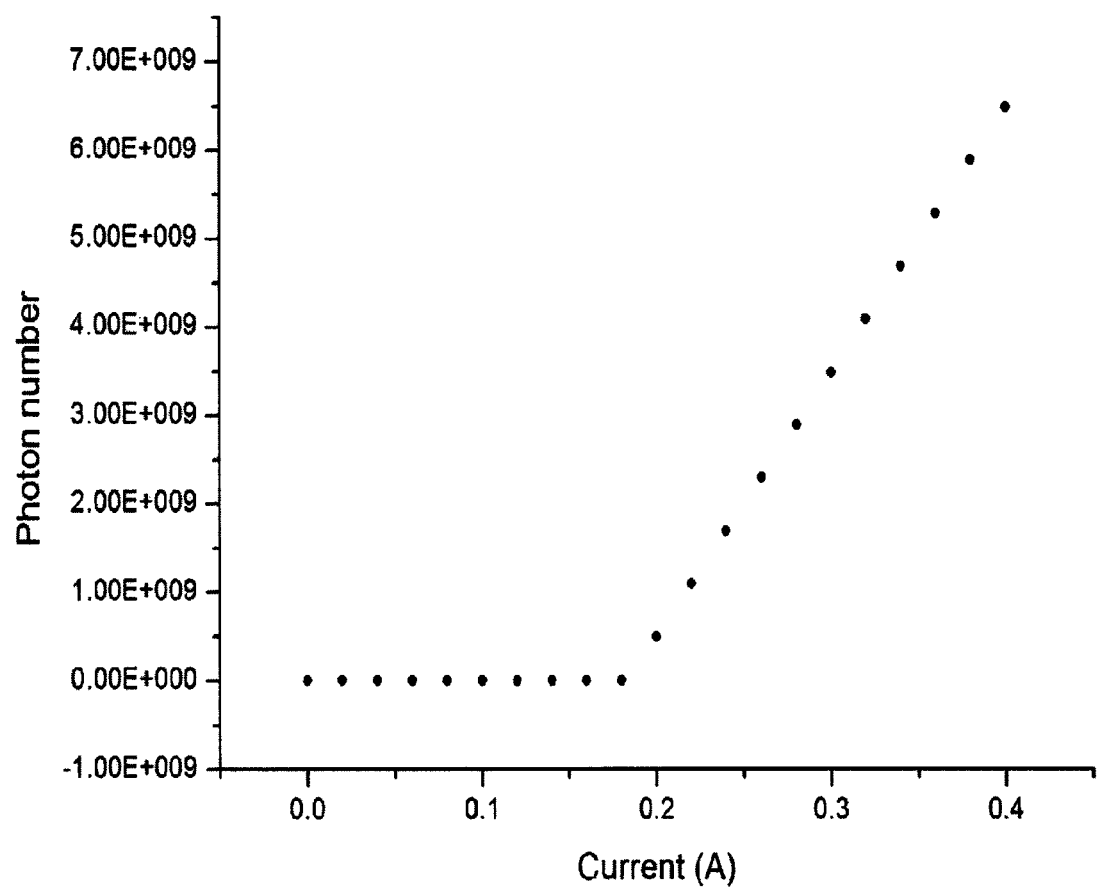
FIG. 13 shows the results of a simulation of an external cavity laser using the rate equations discussed in the text.

A plot of P for A, B and C given by typical values of the model parameters is shown in FIG. 13. The behaviour is qualitatively similar to that observed experimentally in our external cavity QCL system, and is essentially the same as the relationship illustrated in FIG. 2.

Three regions of the plot of FIG. 13 can be identified: the pre-threshold, post-threshold and the threshold itself at ~0.18 A.

In the low-current, pre-threshold region, B<0 and $B^2>>4AC$, from which results the limiting case for the pre-threshold:

$$P_{pre} = -\frac{C}{B}$$

Post-threshold, at high current, the condition $B^2>>4AC$ remains, but B crucially has changed sign. The limiting case is therefore:

$$P_{post} = \frac{|B|}{A} \quad \text{Eq. 2}$$

The threshold is identified as the current for which B=0, from which we obtain the threshold current $I_{thr}$:

$$I_{thr} = \frac{-q\left(\frac{1}{\tau_{32}} + \frac{1}{\tau_{31}}\right)}{\tau_P \tau_{21} Zg\left(\frac{1}{\tau_{32}} - \frac{1}{\tau_{21}} - \frac{\beta}{\tau_e}\right)} \quad \text{Eq. 3}$$

The gradient $$\frac{dP}{dI_{in}}$$

in the post-threshold region is:

$$\frac{dP}{dI_{in}} = \frac{Z\tau_P\left(\frac{1}{\tau_{32}} - \frac{1}{\tau_{21}} - \frac{\beta}{\tau_e}\right)}{q\left(\frac{1}{\tau_{21}} - \frac{1}{\tau_{31}}\right)} \quad \text{Eq. 4}$$

3.2 The Effect of Intracavity Absorption

Within the framework of the rate equation model, the effect of an intracavity absorber is to decrease the photon lifetime, $\tau_p$, as photons are lost from the cavity by absorption. The rate equation for this additional loss due to intracavity absorption is:

$$\frac{dP}{dt_{ICA}} = -P\varepsilon Nc\frac{l}{L}$$

where $\varepsilon$ is the cross-section and N the number density of the intracavity absorber, c is the speed of light, l is the length of cavity occupied by the absorber (e.g. an intracavity cell) and L the total cavity length.

The loss rate $$k_P^\circ = \frac{1}{\tau_P^0}$$

of photons in the presence of an intracavity absorber becomes $$k_P' = \frac{1}{\tau_P^0} + \varepsilon Nc\frac{l}{L} \quad \text{Eq. 5}$$

from which can be defined the photon lifetime in the presence of an intracavity absorber $$\tau_P' = \frac{1}{k_P'}.$$

The effect of intracavity absorption is therefore easily incorporated into the rate equation model outlined in Section 3.1 simply by use of the reduced photon lifetime $\tau'_p$.

Figure 14A:
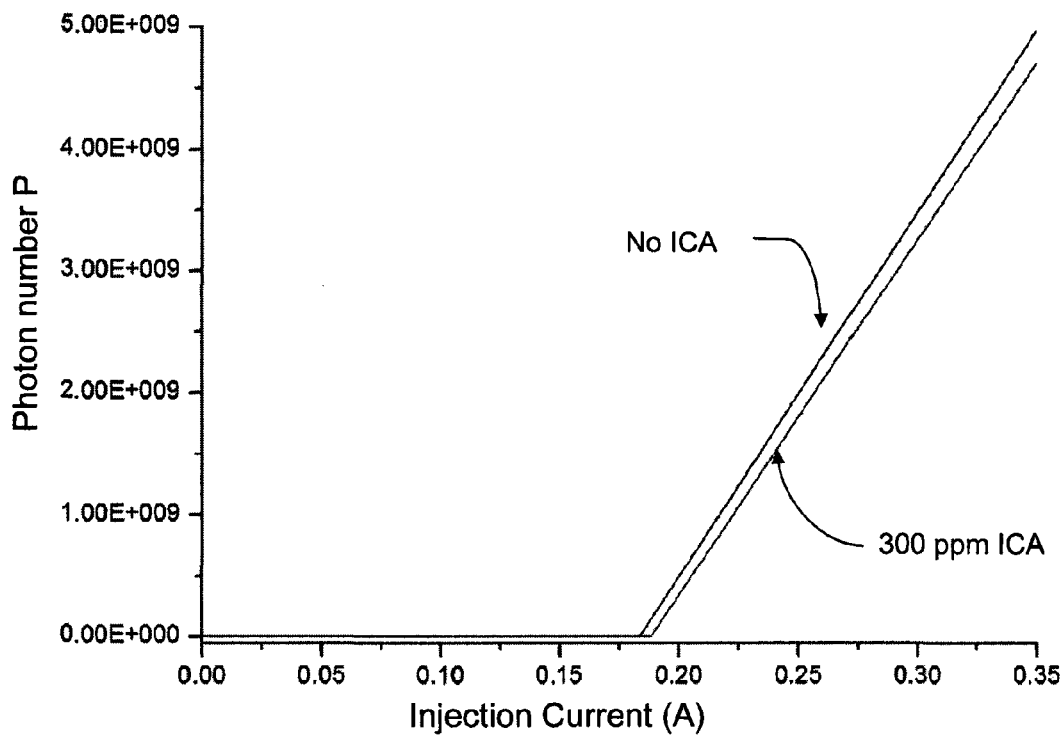
FIG. 14a compares modelling results for laser optical output against injection current in absence of an intracavity absorbing species ("no ICA"), and in the presence of such a species.
Figure 14B:
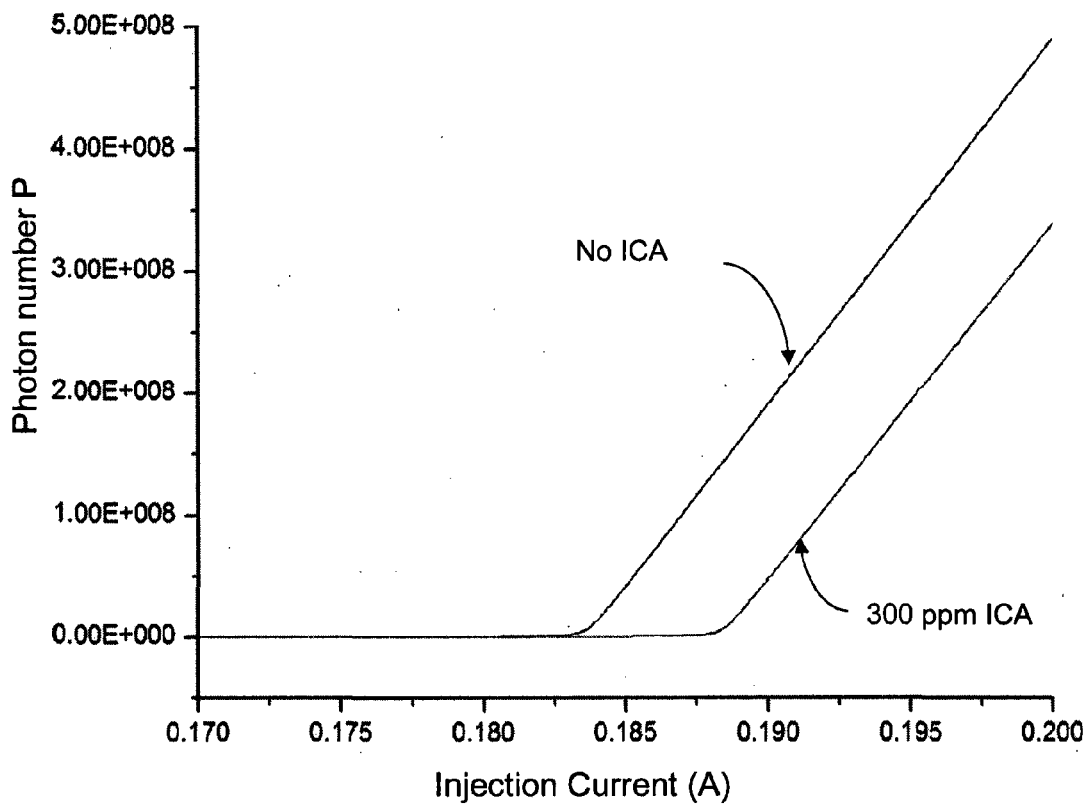
FIG. 14b shows a part of the graph of FIG. 14a expanded along the horizontal axis.

FIGS. 14a and 14b compare the result of the rate equation model with no intracavity absorption to that with 300 ppm of an absorber of absorbance 0.004 $(\text{ppm.m})^{-1}_{10}$ in the intracavity cell, in which the modified photon loss rate constant $k'_p$ is used. Two features are apparent. From FIG. 14a, it can be seen that in the presence of the intracavity absorber (ICA), the post-threshold gradient $dP/dI_{in}$ is reduced, and in FIG. 14b, that the threshold current is increased. FIG. 14b shows the area around the threshold current using an expanded horizontal scale. The change in both gradient and threshold is 2.6%, as predicted by Eqs. 3 and 4 from the values of $\tau_p^\circ$ and $\tau'_p$ given by Eq. 5.

The photon numbers P are taken to be proportional to the measured QCL output intensities for the purpose of evaluating transmission.

The following section illustrates how the behaviour of $P/P_0$ as a function of current is affected by absorber concentration, absorber cross-section and QCL gain. Results are plotted as function of reduced current $I/I_{thr,0}$; $I_{thr,0}$ refers to the threshold current in the absence of absorber. Model parameters are given in Table 1.

Figure 15A:
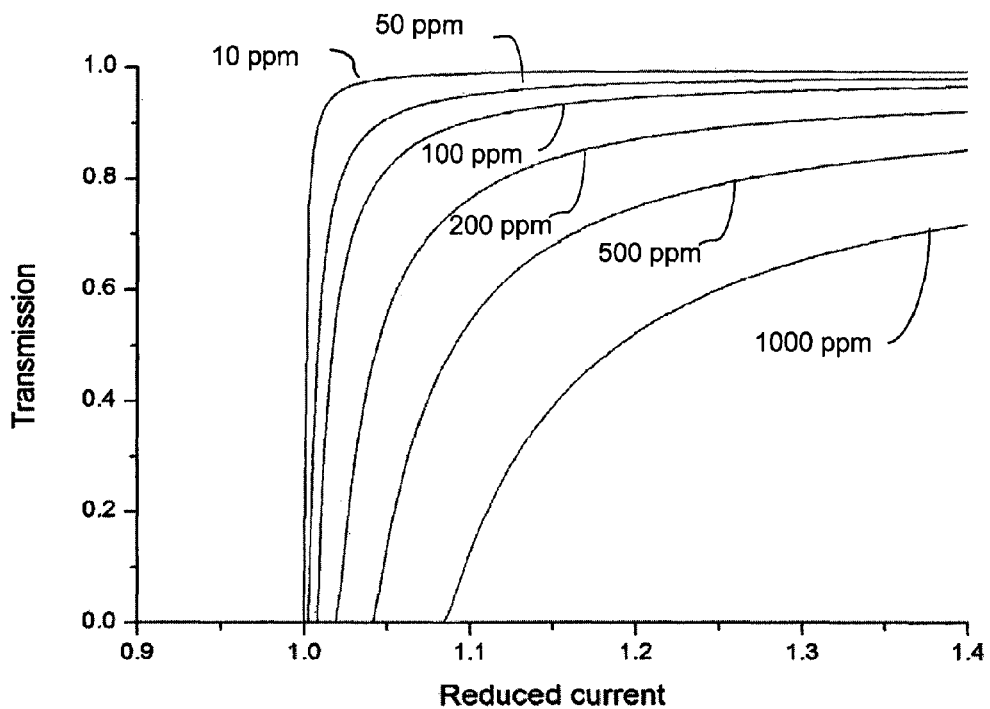
FIG. 15a compares simulated transmission of a sample with varying concentrations of an absorbing species plotted against reduced current, with FIG. 15b showing a part of the graph of FIG. 14a expanded along the horizontal axis.
Figure 15B:
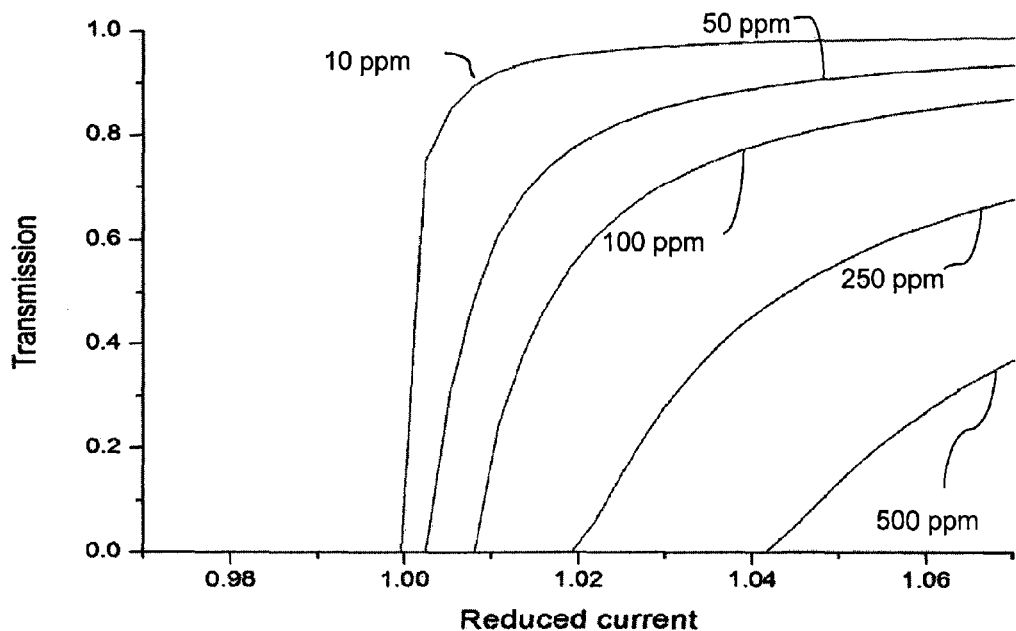

FIGS. 15a and 15b show the simulated behaviour of transmission for varying concentrations of absorber of cross-section $4\times10^{-3}$ $(\text{ppm.m})^{-1}$, with FIG. 15b showing detail around the threshold of FIG. 15a. The figures show that the observed transmission for a given concentration of absorber is a strong function of the laser current, being ~0 just above threshold and rising monotonically to a value close to 1 in the limit of high current. The effect arises because the absorber, rather than absorbing a constant fraction of laser power according to the Beer-Lambert model, has the effect of displacing the threshold to higher currents.

Figure 16:
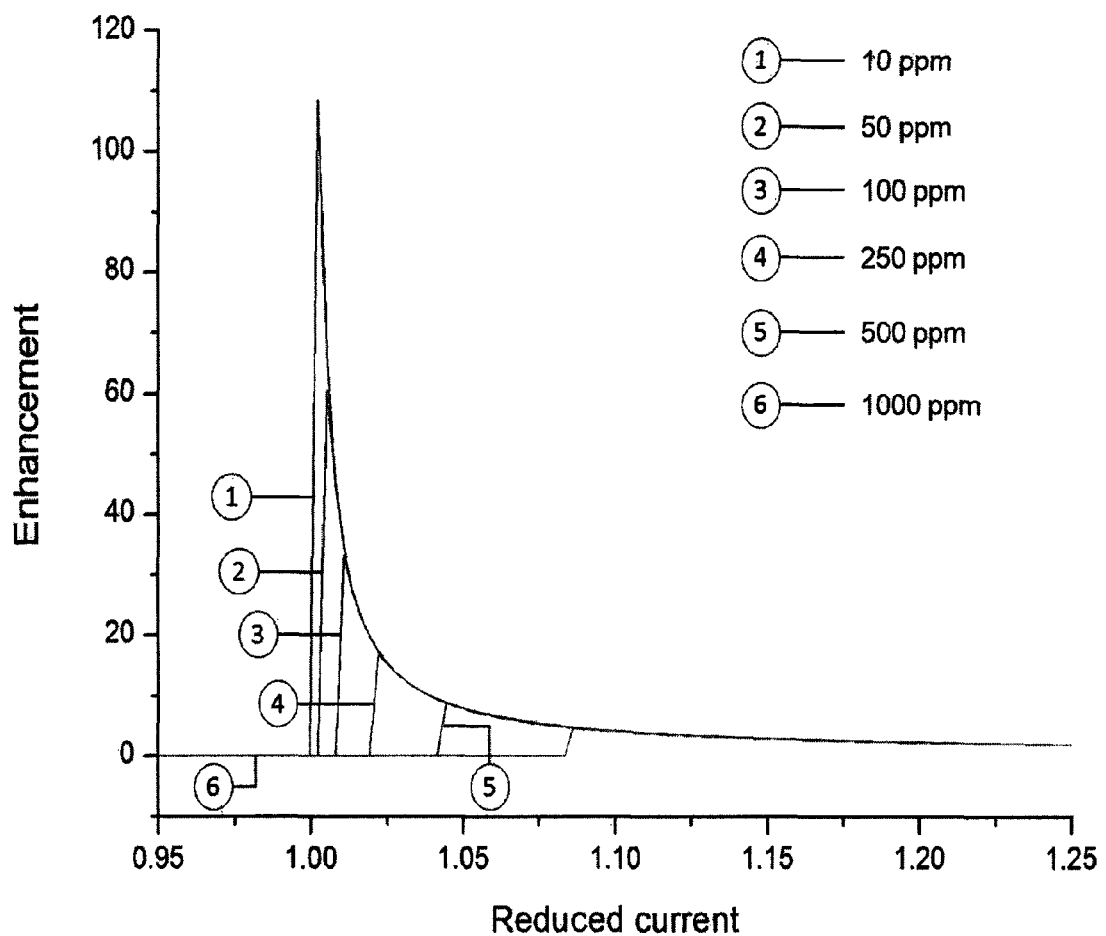
FIG. 16 plots enhancement factors which compare the effect on laser output of the relationship between injection current and laser output with the effect of laser output expected from conventional Beer-Lambert absorption.

The results of the transmission simulations $T_{ICA}$ can be compared to a conventional absorption experiment using the Beer-Lambert transmission $T_{BL}$, calculated as usual as $T_{BL}=\exp(-\varepsilon Nl)$, by defining an 'enhancement factor' $E_{ICA}=T_{BL}/T_{ICA}$. Enhancement factors for the data of FIGS. 15a and 15b and above are shown in FIG. 16.

Enhancement factors for current values below the threshold current for a given absorber concentration have been set to zero.

Similar results are obtained for the variation of transmission and enhancement with absorber cross-section.

Figure 17:
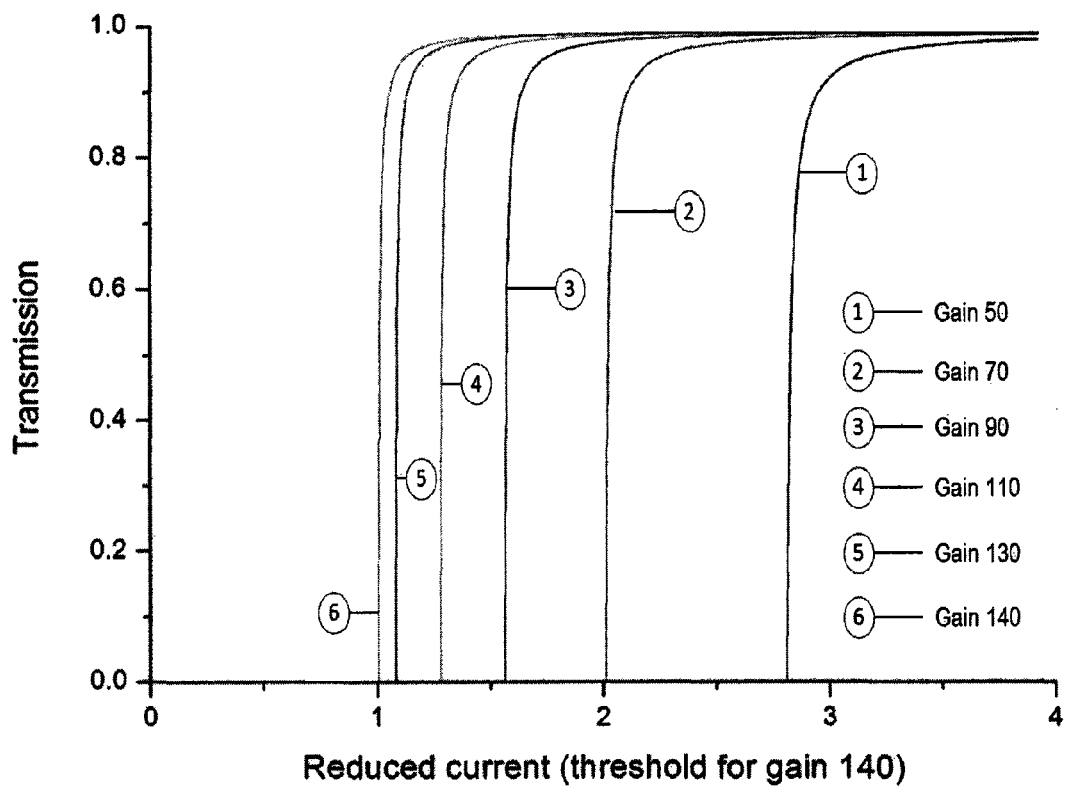
FIG. 17 plots transmission of a sample having an absorbing species against reduced current for a range of laser gains.

Thus far the modelling has been restricted to a single arbitrary value of gain of the semiconductor gain medium 14. In considering how to use the results of the rate equation modelling in interpreting spectra, the variation of gain with wavenumber over the tuning range of the QCL must be considered. FIG. 17 shows the variation of transmission with gain, for which the reduced current has been calculated relative to the threshold current for gain=140, with an ICA having a cross-section of $4\times10^{-3}$ (ppm.m)$^{-1}$ and a concentration 60 ppm.

If the reduced current is alternatively calculated for each gain value relative to the threshold current for that gain, however, the transmission curves for all values of gain are identical.

The full functional form of $P/P_0$ derived from Eq. 1 is cumbersome and not very transparent, and hence of limited use. An alternative is to note the linear dependence of P on I above threshold (from Eq. 2):

$$P = \frac{1}{K_1}\left[\frac{K_{-3}}{\tau_{21}g} + \frac{Z\left(\frac{1}{\tau_{32}} - \frac{1}{\tau_{21}} - \frac{\beta}{\tau_e}\right)}{q}\tau_p I\right]$$

where $$K_1 = \frac{1}{\tau_{21}} + \frac{1}{\tau_{31}}$$

and $$K_{-3} = \frac{1}{\tau_{32}} + \frac{1}{\tau_{31}}.$$

The transmission $P/P_0$ is then $$\frac{P}{P_0} = \frac{K + \gamma\tau'_p I}{K + \gamma\tau_p^o I} \qquad \text{Eq. 6}$$

where $$K = \frac{K_{-3}}{\tau_{21}g}$$

and $$\gamma = \frac{Z\left(\frac{1}{\tau_{32}} - \frac{1}{\tau_{21}} - \frac{\beta}{\tau_e}\right)}{q}$$

Note that the limit of $P/P_0$ at high current is not 1, but $$\frac{\tau'_p}{\tau_p^o}.$$

By writing $\tau'_p = R\tau_p^o$ the transmission can be more conveniently written:

$$\frac{P}{P_0} = \frac{K + R\gamma\tau_p^o I}{K + \gamma\tau_p^o I} \qquad \text{Eq. 7}$$

4. Data Analysis

In the context of the rate equation model, the concentration of an intracavity absorber present in the absorption cavity 20 may be derived fundamentally from the change in photon lifetime brought about by intracavity absorption according to Eq. 5. There are, however, various possible measurement strategies and associated data reduction methods, some of which are now described.

4.1 Transmission Measurements

A means of extracting quantitative concentration measurements from the data of FIG. 11 is provided by Eq. 7, treating K, R and $\gamma\tau''_p$ as fit parameters. Setting physically reasonable initial values for K and $\gamma\tau''_p$ of $8\times10^{10}$ (ps)$^{-1}$ and $-1\times10^{11}$ (pC)$^{-1}$ and allowing R between 0 and 1.1, the values of R (the factor by which the photon lifetime is reduced by the presence of an intracavity absorber) shown in table 2 were obtained.

TABLE 2

Photon lifetime reduction factors R obtained from the data of FIG. 11.

| DMC concentration/ppm | R | Standard deviation |
|---|---|---|
| 10 | 0.99667 | 3.86545E−4 |
| 30 | 0.99192 | 9.60757E−4 |
| 100 | 0.97125 | 0.00242 |
| 300 | 0.92068 | 0.01768 |

Figure 18A:
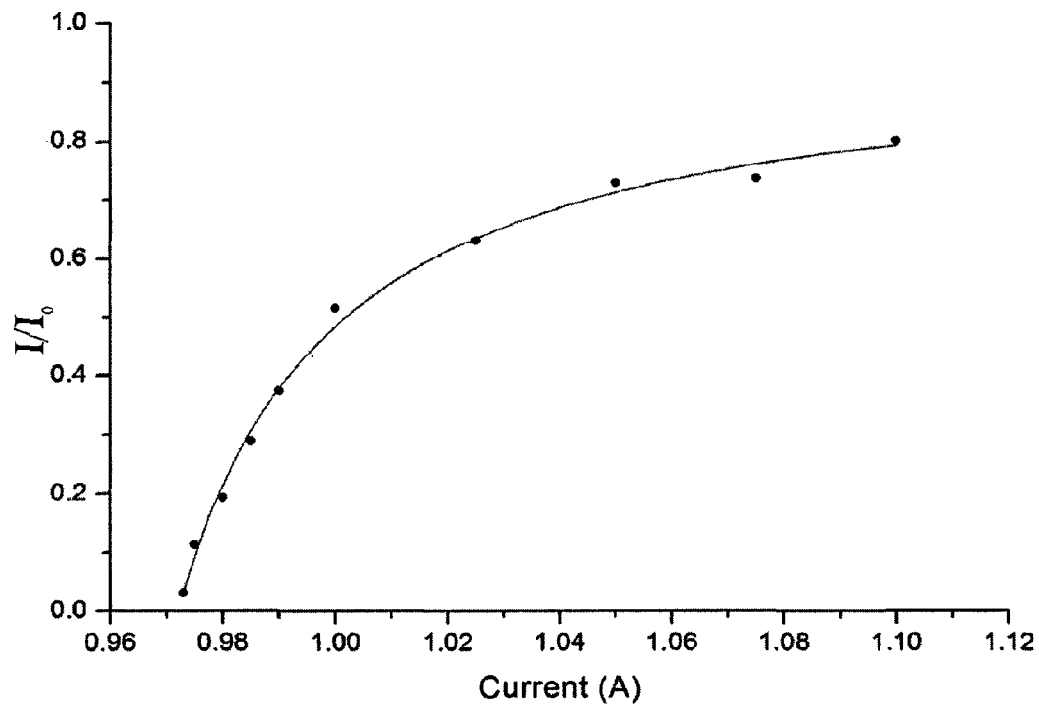
FIG. 18a shows a plot of a non-linear least squares fit of equation 7 to transmission measurements for a 100 ppm dimethyl carbonate sample, to derive a photon lifetime reduction factor.
Figure 18B:
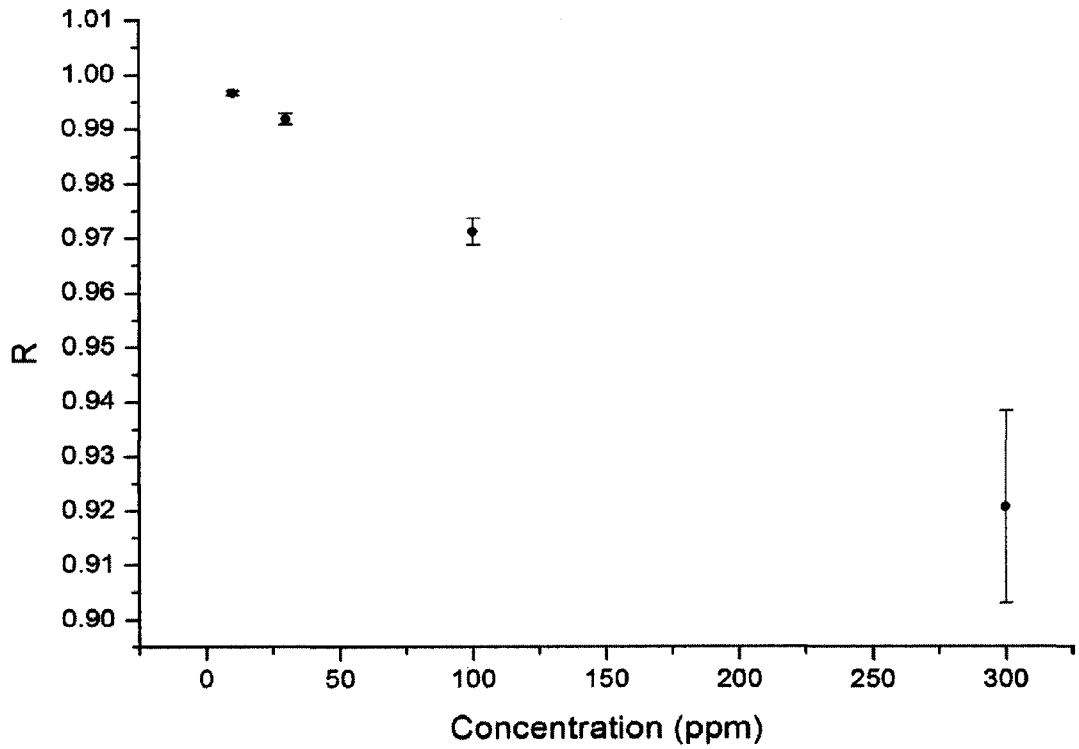
FIG. 18b plots the photon lifetime reduction factors obtained from the data of FIG. 11.

An example of a non-linear least-squares fit of Eq. 7 to transmission measurements for 100 ppm DMC to derive a photon lifetime reduction factor R of 0.97125±0.00242 for a single concentration (100 ppm) is shown in FIG. 18*a*, and from the data of Table 2 with 1σ error bars in FIG. 18*b*.

Figure 19:
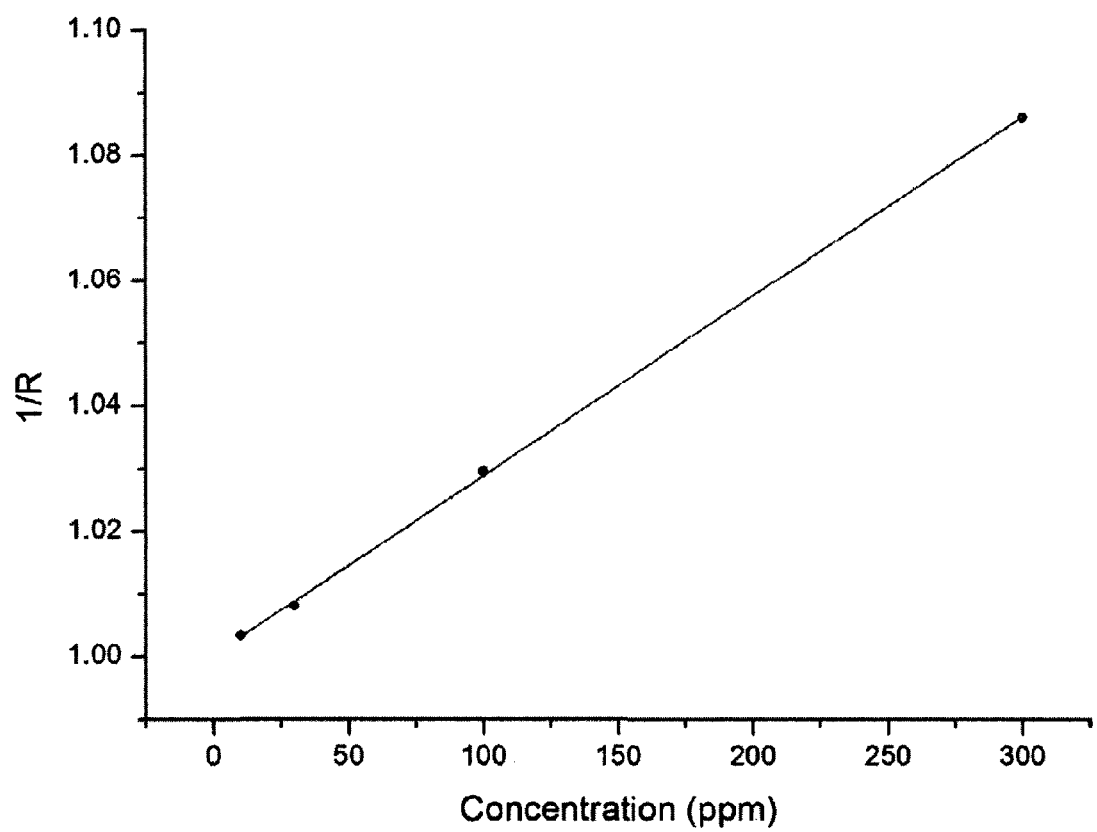
FIG. 19 plots a reciprocal of the photon lifetime reduction factor against a sample concentration of dimethyl carbonate.

The lifetime reduction factor R can be related to the concentration of intracavity absorber by:

$$\frac{1}{R} = 1 + \frac{\varepsilon N c l}{L}\tau_p^o \qquad \text{Eq. 8}$$

from which the concentration N of intracavity absorber can, given a prior measurement of the photon lifetime $\tau_p^o$, be obtained from the slope of plot of 1/R against concentration as shown in FIG. 19 for DMC as the detected species, in which the fitted line for 1/R has a slope of $2.868\times10^{-4}$ and an intercept of 1.00026.

In a practical device, laser output may be measured over a range of injection currents, with and without intracavity absorber, to determine a single value of R. The unknown concentration could then be determined from the R-value using Eq. 9:

$$N = \frac{(1-R)L}{R\varepsilon c l\,\tau_p^o} \qquad \text{Eq. 9}$$

For any given wavelength and state of external cavity alignment the photon lifetime $\tau_p^o$ can be determined by first performing an identical measurement but using known concentrations of a calibration gas.

4.2 Change in Threshold Current

A further means of extracting quantitative concentration measurements, from data such as illustrated in FIG. 12, is provided by measuring the increased threshold current brought about by an intracavity absorber and normalising it to the threshold measured in the absence of intracavity absorption. In this case, from Eq. 3, the ratio of threshold currents is analogous to Eq. 9:

$$\frac{I_{thr}}{I_{thr,0}} = 1 + \frac{\varepsilon N c l}{k_0 L} \qquad \text{Eq. 10}$$

Figure 20:
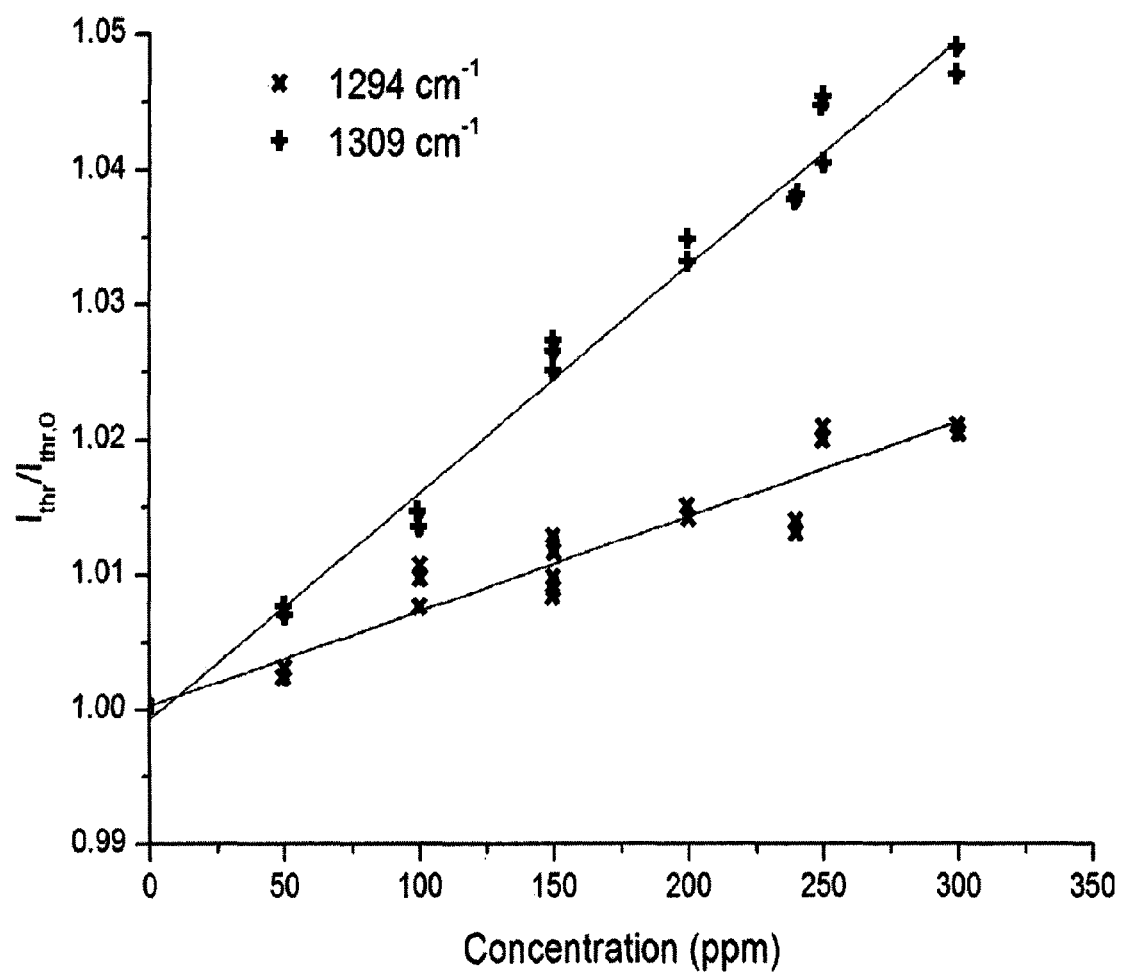
FIG. 20 is a plot of threshold current measurements at two wavelengths as a function of intracavity absorber.

FIG. 20 shows both sets of data taken in the measurements described in section 3.2. There are the threshold current measurements at two wavelengths as a function of concentration of intracavity absorber. Also shown is the linear least-square regression to each set of data, the parameters of which are shown in Table 3.

TABLE 3

Regression parameters from threshold current experiments

| Wavelength/ cm$^{-1}$ | Intercept | Slope/ppm$^{-1}$ | DMC absorbance/ (ppm · m)$^{-1}$ |
|---|---|---|---|
| 1294 | 0.9992 ± 0.0009 | (16.871 ± 0.047) × 10$^{-5}$ | 0.00422 |
| 1309 | 1.0003 ± 0.0008 | (7.053 ± 0.046) × 10$^{-5}$ | 0.00211 |

Eq. 10 predicts that the ratio of the slopes at the two wavelengths should be equal to the ratio of absorbances. For the data of FIG. 20 and table 3 these ratios are 2.39 and 2 respectively, corresponding to a fractional error of ~20%. The results support the validity of the threshold current methodology and show that it can be used to detect a few tens of ppm of a moderate IR absorber at the ~10% accuracy level.

Figure 21:
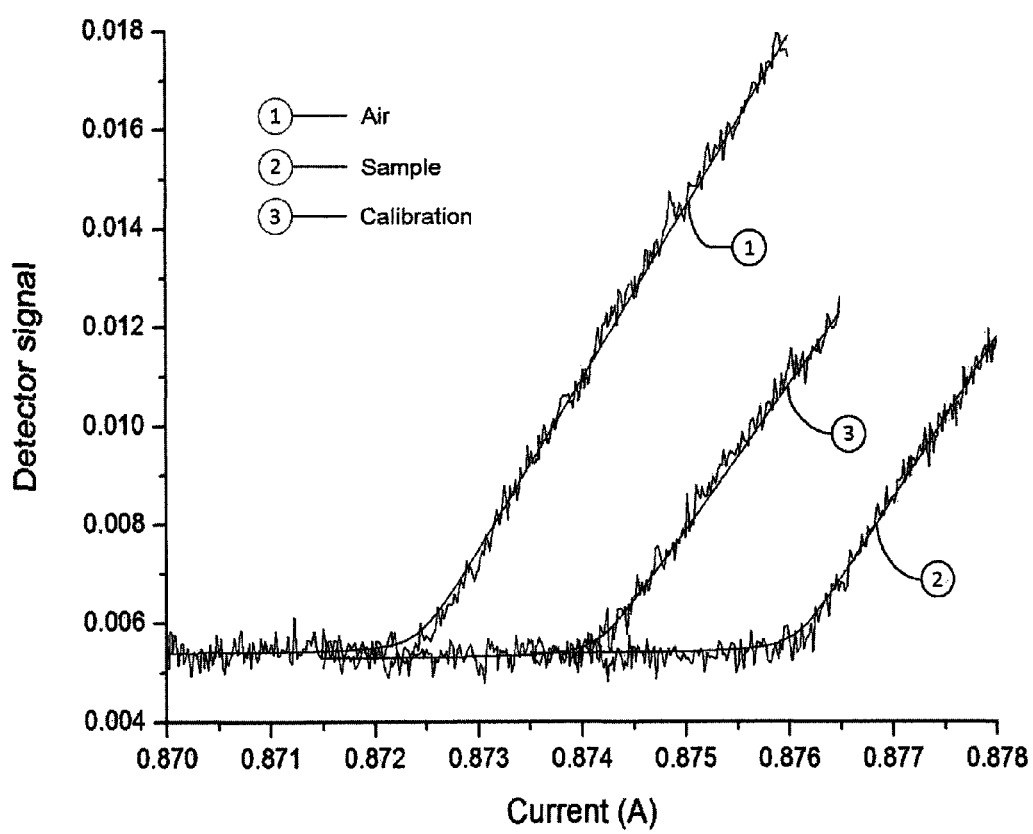
FIG. 21 is a plot of laser output power behaviour around threshold for different contents of the absorption cell.

In an alternative implementations and as mentioned above in connection with FIGS. 6 and 7, the threshold current may be swept repeatedly over a short range, for example centred on the threshold current, allowing sensitivity improvement through signal averaging. In one example of this, at a given wavelength selected by the diffraction grating 50, three traces of laser power versus current were recorded with the cell containing air (which does not absorb at the chosen wavelength), the sample gas, and a calibration gas of known concentration respectively. An example of the three traces of laser power behaviour around threshold is shown in FIG. 21, in which the calibration and sample gases are a 50 and 100 ppm mixture of dimethyl carbonate in 1 atm $N_2$.

Figure 22:
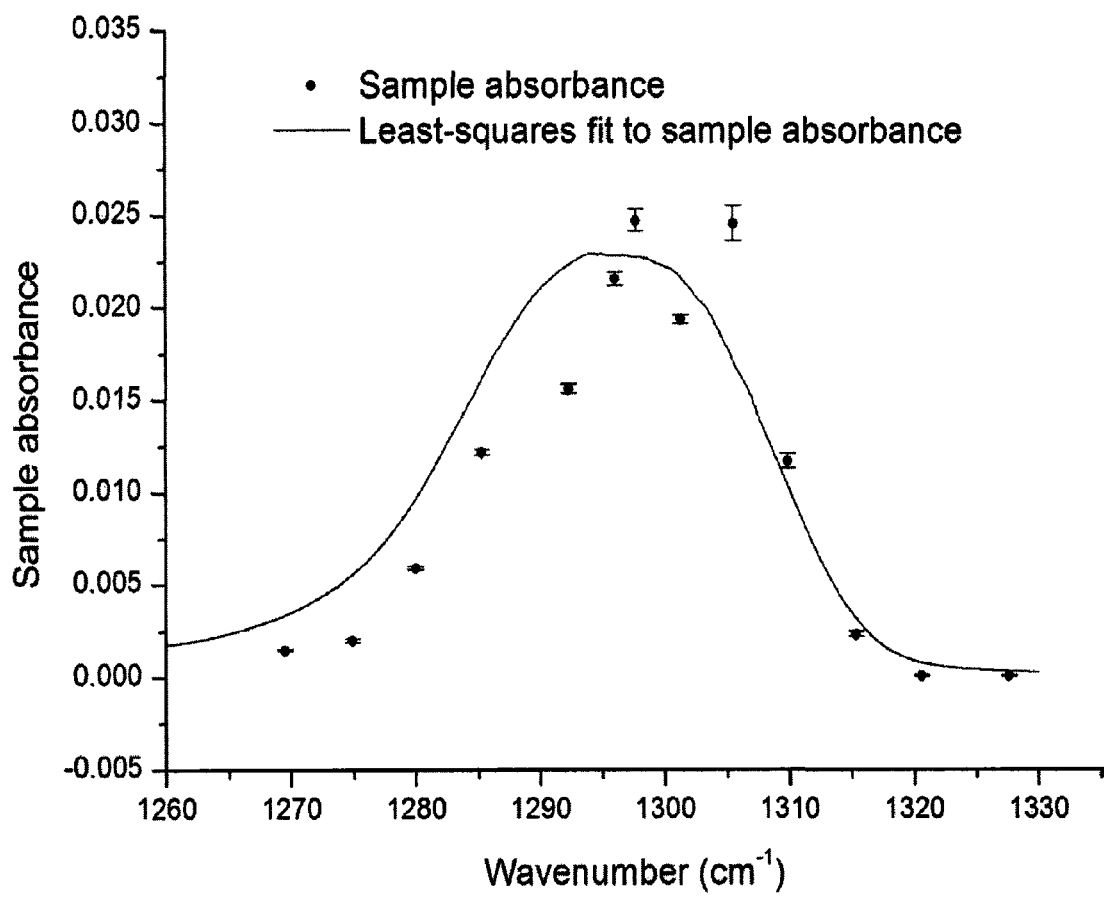
FIG. 22 is a plot of sample absorbance measurements for dimethyl carbonate in the 1270-1320 $cm^{-1}$ laser wavelength region made using the described apparatus.

Eqn. 1 may be re-cast for use as a non-linear least-squares fitting function in which one of the fit parameters, R', represents the fractional change in threshold current in the absence of absorption, $I_{thr,0}$, brought about by an intracavity absorber; R' for the fit to the air sample trace is constrained to unity (by definition) in order to determine $I_{thr,0}$, which is constrained in subsequent fits to the sample and calibration gas traces. The R' values derived from each fit are then used to determine the absorbance of the unknown sample. By repeating the process at different wavelengths, the absorbance spectrum of the sample is obtained. An example for dimethyl carbonate is shown in FIG. 22. The measured sample absorbance at 13 wavelengths in the 1270-1320 cm$^{-1}$ region is shown, with error bars; the solid line represents a linear least squares fit of the known absorption spectrum of dimethyl carbonate in which the concentration is the fit parameter. The fitted concentration is 118±14 ppm, compared to the true value of 100 ppm.

Figure 23:
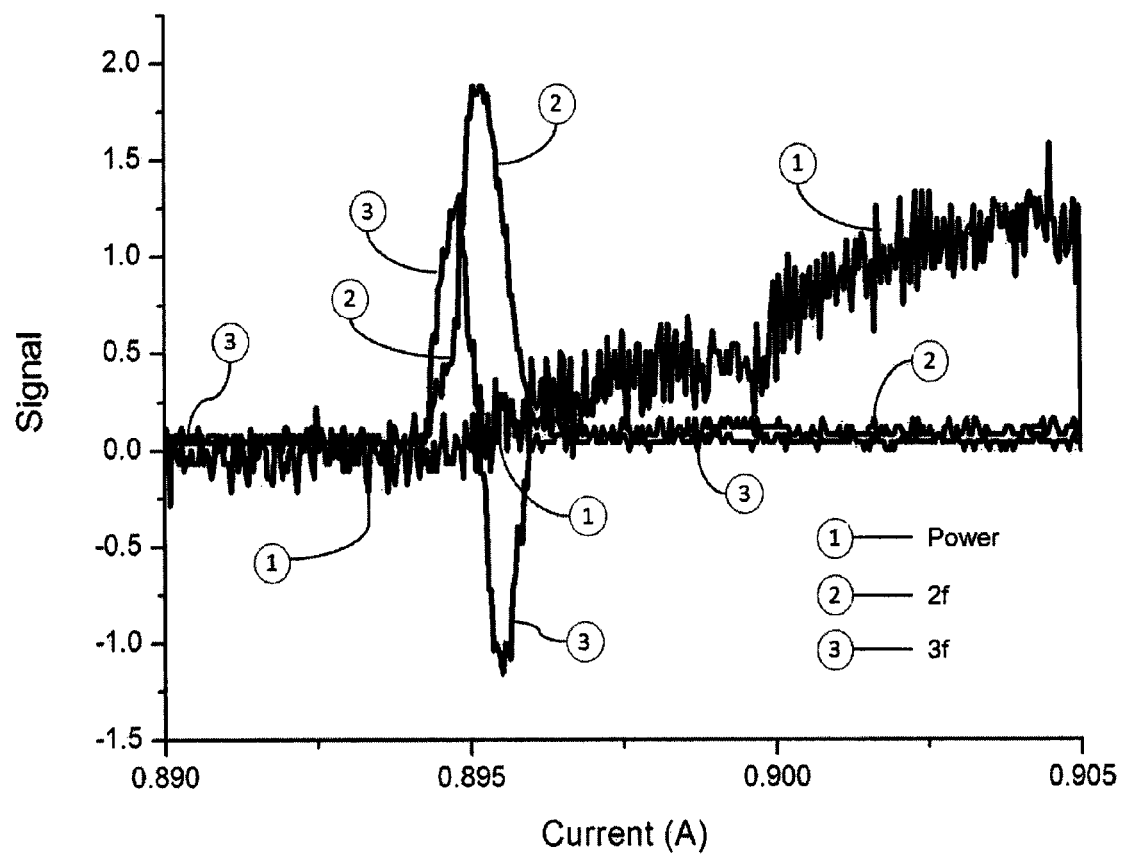
FIG. 23 is a plot of laser power and second and third derivative signals of laser power with respect to injection current obtained from a lock-in amplifier, for example using apparatus as described in connection with FIG. 7b.

In other embodiments, current may be ramped over the laser threshold in a manner described in connection with FIG. 21 whilst simultaneously applying a small (~1 mA) sinusoidal modulation. A lock-in amplifier may then be used to detect and record the second (2f) and third (3f) derivative signal of the laser power. FIG. 23 shows an example of the laser power and the two derivatives.

Consideration of the rate equation model simulation of FIGS. 14a and 14b shows that the second derivative signal reaches a maximum at the point of inflection of the power trace. The threshold current can therefore now also be obtained by fitting a peak function to the second derivative. In the example above, the rate equation model fit gives $I_{thr}$=894.2±0.24 mA (1σ), and the second derivative fit (arbitrarily using a Gaussian as the peak function) gives $I_{thr}$=895.2±0.004 mA (1σ). The precision of the fit to the second derivative corresponds to a sensitivity of ≈10$^{-5}$ in absorbance, though for the apparatus described in respect of FIG. 3, temporal threshold instability is expected to lead to a reduction in sensitivity. Allan variance analysis shows that by suitable choice of averaging period, the reduction is a factor of ≈3.

If the third harmonic signal is of suitable size and form to be used as an error signal in a control loop, in which the central point, $I_0$, about which the injection current, I, is ramped is held at the maximum of the second derivative signal; $I_0$ is thus a direct measurement of the threshold current. Compared to the rate equation fitting method described earlier, the advantages of using this method in a practical device are:
  (i) Threshold current can be read directly, circumventing the need for fitting
  (ii) Reduced sensitivity to mode hops non-linearity of laser power above threshold, by virtue of lock-in amplifier bandwidth
  (iii) Up to 2 orders of magnitude improvement in precision of $I_{thr}$ measurement 5. Sensitivity The sensitivity enhancement of the methods and apparatus described above over conventional Beer-Lambert absorption is not straightforward to quantify because the two methods are qualitatively different. However, some examples serve to illustrate the advantage of the currently described invention:
  (1) Using a photon lifetime from the R-value determined in section 4.1 for 100 ppm DMC to calculate the concentration (imagined to be unknown) of DMC used in the 10 ppm data set, a concentration of 11.3±0.35 ppm is deduced. Compared to the true concentration of 10 ppm the measurement is accurate to 13%. A similar calculation for the 30 ppm data gives 27.5±0.35 ppm, an accuracy of 9%. Assuming that a conventional absorption measurement has absolute sensitivity of ≈1%, a measurement with a fractional accuracy of 10% requires an absolute absorption of 10%. Using the described intracavity cell for such an absorption measurement would require ≈550 ppm DMC. The enhancement factor is therefore at least 55.
  (2) From FIG. 11 it can be seen that by suitable choice of injection current, absorption values of 90% and 50% can reliably be made for 100 and 30 ppm DMC respectively. Calculation of the Beer-Lambert absorptions gives only 2% and 0.6% respectively, corresponding to enhancements of factors of ≈45 and ≈83 respectively.
  (3) Though not statistically rigorous, a measure of the sensitivity of the threshold measurement methodology can be found by from Table 3 by calculating the concentration of intracavity absorber required to cause an increase in I/$I_{thr}$ greater than the standard deviation of the intercept; this concentration is ≈6 ppm, corresponding to an enhancement of ≈90

Although specific detailed embodiments of the invention have been described, the skilled person will appreciate that various modifications and variations can be made without departing from the scope of the invention as defined in the claims. For example, instead of using a Littrow grating configuration for the diffraction grating 50, other configurations such as a Littman-Metcalf configuration could be used.

The invention claimed is:

1. Apparatus arranged to determine one or more characteristics of a sample in an absorption cell, the apparatus comprising:
   an external cavity semiconductor laser comprising a semiconductor gain medium within an optical resonator;

said absorption cell being arranged such that at least part of the sample in the absorption cell is within the optical resonator and is optically coupled with the gain medium;
a controller arranged to vary an injection current applied to the semiconductor gain medium;
a photo detector arranged to detect laser light output by the external cavity semiconductor laser; and
an analyser arranged to determine one or more characteristics of the sample from behaviour of the detected laser light output as a function of the varied injection current.

2. The apparatus of claim 1 wherein the external cavity semiconductor laser comprises a wavelength selector arranged to selectively tune the laser to each of a plurality of wavelengths, and the analyser is arranged to determine one or more characteristics of the sample at each selected wavelength from behaviour of the detected laser light output as a function of the varied injection current at or proximal to each selected wavelength.

3. The apparatus of claim 2 wherein the wavelength selector is a diffraction grating forming a boundary of the optical resonator.

4. The apparatus of claim 3 wherein the diffraction grating is mounted in a first order Littrow configuration with respect to the optical resonator.

5. The apparatus of claim 1 wherein the one or more characteristics of the sample comprise an absorption spectrum of the sample.

6. The apparatus of claim 1 wherein the one or more characteristics of the sample comprise one or more concentrations of one or more species within the sample.

7. The apparatus of claim 1 wherein the external cavity semiconductor laser is a quantum cascade laser.

8. The apparatus of claim 1 wherein the analyser is arranged to determine said one or more characteristics of the sample at least partly from one or more determinations of a laser threshold current of said injection current.

9. The apparatus of claim 8 arranged to determine a laser threshold current from a second derivative of the laser output power with respect to the injection current.

10. The apparatus of claim 1 wherein the analyser is arranged to determine said one or more characteristics of the sample at least partly from one or more gradients of the detected laser light output laser as the injection current is varied above a laser threshold current.

11. The apparatus of claim 1 wherein the controller is arranged to modulate the injection current.

12. The apparatus of claim 11 wherein the controller is additionally arranged to ramp the injection current such that the ramp encompasses the concurrent threshold current.

13. A method of determining one or more characteristics of a sample comprising:
locating the sample in the optical cavity of an external cavity laser such that the sample is optically coupled with a gain medium of the external cavity laser;
applying a varying injection current to drive the gain medium;
detecting laser light output by the external cavity laser; and
determining said one or more characteristics of the sample from behaviour of the detected laser light as a function of the applied variations in injection current.

14. The method of claim 13 further comprising:
using a wavelength selector to vary tuning of the external cavity laser across a wavelength range; and
determining said one or more characteristics as functions of wavelength.

15. The method of claim 13 wherein determining said one or more characteristics as functions of wavelength comprises determining an absorption spectrum of the sample.

16. The method of claim 13 wherein determining said one or more characteristics comprises identifying and/or determining concentrations of one or more species within the sample.

17. The method of claim 13 wherein determining said one or more characteristics of the sample from behaviour of the detected laser light as a function of the applied variations in injection current comprises detecting a threshold current of the external cavity laser and using said threshold current in said step of determining.

18. The method of claim 13 wherein the gain medium is a quantum cascade laser gain medium, the external cavity laser is a quantum cascade external cavity laser, and the sample is a gaseous sample.

19. The method of claim 13 wherein the sample is retained within an absorption cell at least partially containing the optical cavity of the external cavity laser.

20. A method of determining one or more absorption characteristics of a sample comprising:
disposing the sample in an optical cavity of an external cavity laser having a gain medium, such that the sample gives rise to a loss rate of photons generated in the gain medium; and
determining said one or more characteristics from a change in photon lifetime of the external cavity laser in the presence of the sample.

21. The method of claim 20 wherein the change in photon lifetime is detected from behaviour of the external cavity laser with respect to an injection current applied to the gain medium.

22. The method of claim 21 wherein the behaviour of the external cavity laser with respect to an injection current applied to the gain medium is detected by measuring optical output of the external cavity laser.

23. The method of claim 20 wherein the change in photon lifetime is a reduction in photon lifetime in comparison to absence of said sample.

* * * * *